US011191904B2

(12) United States Patent
Jazayeri et al.

(10) Patent No.: US 11,191,904 B2
(45) Date of Patent: Dec. 7, 2021

(54) PLUNGERS FOR DRUG DELIVERY DEVICES

(71) Applicant: AMGEN INC., Thousand Oaks, CA (US)

(72) Inventors: Julian Jazayeri, Woodland Hills, CA (US); Ronald Forster, Simi Valley, CA (US); Jolita Seckute, Thousand Oaks, CA (US); Olivia Alice Henderson, Newbury Park, CA (US); Kristen Brown, Ventura, CA (US); Gregory Gordon, Moorpark, CA (US); Rasmus Øhlenschlæger, Copenhagen V (DK); Peter Dan Kaare Soelberg, Gentofte (DK)

(73) Assignee: AMGEN INC., Thousand Oaks, CA (US)

( * ) Notice: Subject to any disclaimer, the term of this patent is extended or adjusted under 35 U.S.C. 154(b) by 195 days.

(21) Appl. No.: 16/154,759

(22) Filed: Oct. 9, 2018

(65) Prior Publication Data

US 2019/0143047 A1 May 16, 2019

Related U.S. Application Data

(60) Provisional application No. 62/584,335, filed on Nov. 10, 2017.

(51) Int. Cl.
*A61M 5/31* (2006.01)
*A61M 5/315* (2006.01)
(Continued)

(52) U.S. Cl.
CPC .... *A61M 5/31513* (2013.01); *A61M 5/14244* (2013.01); *A61M 5/14248* (2013.01);
(Continued)

(58) Field of Classification Search
CPC .......... A61M 5/31513; A61M 5/14248; A61M 5/14244; A61M 5/20; A61M 5/2053;
(Continued)

(56) References Cited

U.S. PATENT DOCUMENTS 5,353,691 A 10/1994 Haber et al.
6,053,895 A 4/2000 Kolberg et al.
(Continued)

OTHER PUBLICATIONS

International Application No. PCT/US2018/054904, International Search Report and Written Opinion, dated Jan. 17, 2019.

*Primary Examiner* — Amber R Stiles
(74) *Attorney, Agent, or Firm* — Marshall, Gerstein & Borun LLP

(57) ABSTRACT

A plunger configured as described herein provides geometry optimizations to minimize friction magnitude and variability during use by maintaining low deformation under large extrusion forces. More specifically, plunger embodiments described herein minimize a contact area between the plunger and a syringe or chamber, while also maintaining high contract pressures to maintain container closure integrity. Moreover, the plunger embodiments are configured to have minimal or no increase in the contact area under high loads associated with the delivery of viscous products.

27 Claims, 21 Drawing Sheets

(51) Int. Cl.
*F16J 1/00* (2006.01)
*A61M 5/142* (2006.01)
*A61M 5/20* (2006.01)

(52) U.S. Cl.
CPC ............ *A61M 5/20* (2013.01); *A61M 5/2053* (2013.01); *F16J 1/003* (2013.01); *A61M 2005/3117* (2013.01)

(58) Field of Classification Search
CPC .......... A61M 2005/3117; A61M 5/315; A61M 5/31511; A61M 2005/31516; F16J 1/003
See application file for complete search history.

(56) References Cited

U.S. PATENT DOCUMENTS

| | | | |
|---|---|---|---|
| 2011/0092915 A1* | 4/2011 | Olson | A61M 5/3129 604/198 |
| 2015/0190588 A1* | 7/2015 | Hanson | A61M 5/36 604/123 |
| 2016/0033042 A1 | 2/2016 | Minagawa | |
| 2016/0082193 A1* | 3/2016 | Laubach | A61M 5/31513 604/222 |
| 2016/0175515 A1* | 6/2016 | McCullough | A61M 5/00 604/65 |
| 2017/0246399 A1* | 8/2017 | Forlani | A61M 5/31568 |
| 2018/0243508 A1 | 8/2018 | Berg et al. | |

* cited by examiner

PLUNGERS FOR DRUG DELIVERY DEVICES

CROSS-REFERENCE TO RELATED APPLICATION

The priority benefit of U.S. Provisional Patent Application No. 62/584,335, filed Nov. 10, 2017, is claimed, and the entire contents thereof are expressly incorporated herein by reference.

FIELD OF THE DISCLOSURE

The present disclosure generally relates to plungers and, more particularly, to plungers for drug delivery products.

BACKGROUND

Highly viscous products are being increasingly used in automatic delivery devices, such as autoinjectors and on-body injectors. Automatic delivery devices typically have requirements related to drug delivery time. When using high viscous products, however, the automatic delivery devices require large driving forces to attain required drug delivery times. Additionally, automatic delivery devices can have drive mechanisms that are spaced from plungers within the devices and that deliver up to five times the sustained injection force during initial impact and through drug delivery.

Some conventional plungers have a cylindrical side surface that slides along and seals with the syringe or reservoir of the delivery device. Large driving forces apply a large axial compressive force on the conventional plunger and this can cause the conventional plunger to deform radially outward during extrusion. Such radial deformation can increase the contact area between the plunger and the syringe or reservoir, resulting in greater friction and unpredictability in the extrusion process.

SUMMARY

The present disclosure sets forth plungers, drug delivery assemblies, drug delivery devices, and related methods embodying advantageous alternatives to conventional plungers and methods, and that may address one or more of the challenges or needs mentioned herein, as well as provide other benefits and advantages.

In some embodiments, a plunger for use in a drug delivery device is described herein that includes a body portion having a generally cylindrical sidewall, a leading surface, and a trailing surface. The plunger further includes a plurality of ribs that project radially outwardly from the sidewall of the body portion and are spaced axially apart from one another by recessed side surfaces. The plurality of ribs include at least a trailing rib, a leading rib, and an intermediate rib, where each of the ribs have an annular configuration. The body portion is configured to occupy a first configuration in the absence of an axial load, and a second configuration in the presence of an axial load, where the first and second configurations have a substantially equal radial dimension and the second configuration has an axial dimension that is less than an axial dimension of the first configuration.

The plunger can further include one or more of the following: a trim edge of the body portion can be adjacent to the trailing surface thereof, where the trim edge can further have an outer diameter less than outer diameters of the ribs; the leading surface of the plunger can include a roughened portion and/or have a generally cone-shaped configuration; one or both of the trailing rib and the intermediate rib can be axially smaller than the leading rib; at least one of the ribs can have a curved profile; at least one of the ribs can include a cylindrical portion extending between curved, axial end portions thereof; radial surfaces of the sidewall extending between the ribs can have curved configurations; radial surfaces of the body portion extending between the ribs can have flat configurations; or the plunger can further include a plurality of protrusions extending away from the trailing surface of the body portion.

In several embodiments, a drug delivery assembly is described herein that includes the plunger configured as recited in any combination of the above paragraphs, where the drug delivery assembly includes: a chamber with an annular sidewall extending between a first, open end and a second end having a dispensing opening, the plunger received within the chamber so that the ribs thereof seal against an interior surface of the sidewall; and a drive member configured to drive the plunger through the chamber to the second end thereof.

The drug delivery assembly can further include one or more of the following: a contact area of the ribs on the sidewall interior remains substantially constant while the plunger is driven through the chamber; a trim edge of the plunger is spaced from the sidewall interior while the plunger is driven through the chamber; the ribs are axially spaced apart from one another at least double a distance of plunger travel within the chamber during air transport; or the ribs have at least a 0.8 MPa contact pressure with the sidewall interior.

BRIEF DESCRIPTION OF THE DRAWINGS

The above needs are at least partially met through provision of the plunger embodiments described in the following detailed description, particularly when studied in conjunction with the drawings, wherein.

Figure 1:
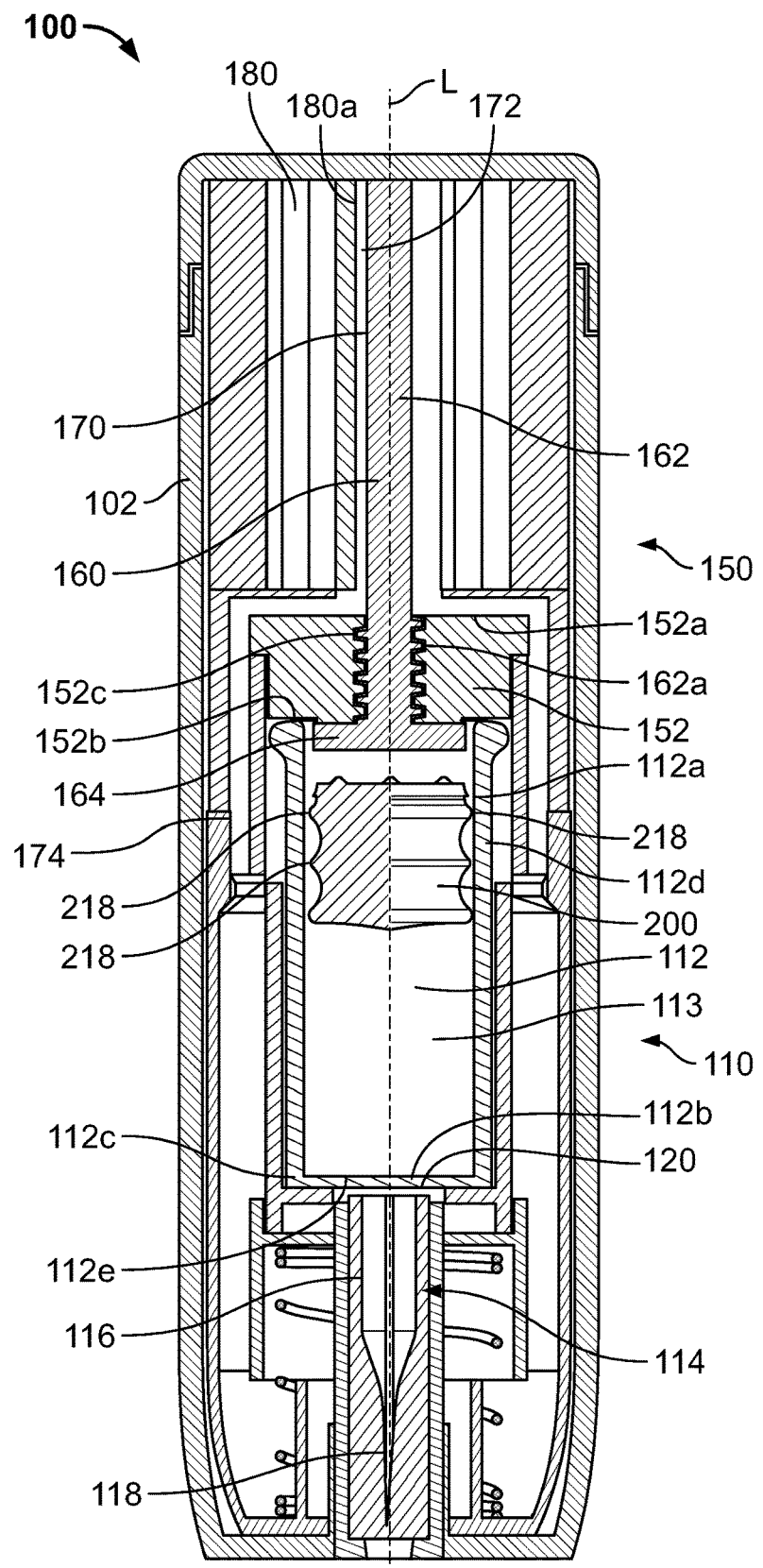
FIG. 1 is a cross-sectional, side elevation view of an autoinjector device including a plunger constructed in accordance with various embodiments of the present disclosure.

Skilled artisans will appreciate that elements in the figures are illustrated for simplicity and clarity and have not necessarily been drawn to scale. For example, the dimensions and/or relative positioning of some of the elements in the figures may be exaggerated relative to other elements to help to improve understanding of various embodiments of the present invention. Also, common but well-understood elements that are useful or necessary in a commercially feasible embodiment are often not depicted in order to facilitate a less obstructed view of these various embodiments. It will further be appreciated that certain actions and/or steps may be described or depicted in a particular order of occurrence while those skilled in the art will understand that such specificity with respect to sequence is not actually required. It will also be understood that the terms and expressions used herein have the ordinary technical meaning as is accorded to such terms and expressions by persons skilled in the technical field as set forth above except where different specific meanings have otherwise been set forth herein.

DETAILED DESCRIPTION

Plungers, also known as plunger-stoppers or stoppers, configured as described herein provide geometry optimizations that minimize friction magnitude and variability during use as compared to conventional plungers by providing low radial and contact area deformation under large extrusion forces. Additionally, plunger embodiments described herein minimize a contact area between the plunger and a syringe or reservoir by utilizing ribs rather than a cylindrical side contact surface, while also maintaining high contact pressures between the ribs and the syringe/reservoir to maintain container closure integrity. Further, the plunger embodiments described herein are configured to have minimal or no increase in the contact area under high loads associated with the delivery of viscous products, i.e., the ribs and the plunger surface extending therebetween do not expand outwardly during use, or expand a minimal amount, to thereby maintain consistent contact area during use. By some approaches, the plungers include three or more radial ribs that maintain a seal with the syringe or chamber, while also avoiding breaches in sterility during storage and transportation, such as due to pressure changes.

Combinations of these features advantageously not only provide low friction magnitude and variability during use as compared to conventional plungers, but also provide up to a 30% injection time reduction over conventional plungers. Low friction variability further provides a more robust design space, which enables the development of high viscosity drug delivery devices, such as autoinjectors and on-body injectors.

Autoinjector Disclosure

Before providing further details of the plunger embodiments, an example drug delivery device will be described with reference to FIG. 1 that is suited for the delivery of high viscous products. In a first example, an autoinjector 100 includes a housing 102 having a syringe assembly 110 and an actuating mechanism 150. At least a portion of the syringe assembly 110 and the actuating mechanism 150 are disposed within the housing 102. The syringe assembly 110 includes a syringe barrel 112, a needle assembly 114, and an optional filter member 120 disposed adjacent to the needle assembly 114. The actuating mechanism 150 includes a frame member 152, a plunger assembly 160 including a plunger 200 described in more detail below, a plunger rod guide 170, a spiral torsion spring (e.g., a watch spring) 180.

The syringe barrel 112 stores a medicament 113 to be injected into a user, and has a first end 112a, a second end 112b, and a longitudinal axis "L". In the illustrated example, the syringe barrel 112 further includes a base 112c and a sidewall 112d that define a cavity to store the medicament. Further, the syringe barrel 112 may include at least one opening 112e disposed through the base 112c to allow the medicament to pass into the needle assembly 114. The first end 112a of the syringe barrel 112 may be open to accommodate the plunger assembly 160, which will be described in further detail below.

It is understood that the syringe barrel 112 may be any desired shape and/or size to accommodate various quantities of medicament. In some examples, the syringe barrel 112 can be constructed from a cyclic-olefin polymer ("COP"). Other examples of materials are possible.

With reference to FIG. 1, the needle assembly 114 is coupled to the second end 112b of the syringe barrel 112 via any type of coupling mechanism and/or structure, and includes a needle hub 116 and a needle 118 attached thereto. The needle hub 116 defines a cavity that allows medicament to enter into the needle 118 via any number of openings. The needle hub 116 is positioned below the opening 112e formed in the base 112c of the syringe barrel 112. So configured, the needle hub 116 receives the medicament as it exits the syringe barrel 112, which then enters into the needle 118 to be administered to the user. It is understood that the injector 100 may include any number of additional components such as return springs, needle shields and/or guards, and the like to assist in administering the medicament to the user. For the sake of brevity, these additional components will not be discussed in substantial detail.

With continued reference to FIG. 1, the filter member 120 is disposed adjacent to the syringe barrel 112 and the needle assembly 114. In some examples, the filter member 120 may be disposed directly within the opening 112e formed in the base 112c of the syringe barrel 112. In other examples, the filter member 120 may be disposed within a portion of the cavity defined by the needle hub 116, distally beyond the base 112c of the barrel 112. In yet other examples, the filter member 120 may be positioned between the base 112c of the syringe barrel 112 and the needle hub 116. Alternatively, the filter member 120 may be positioned within the syringe barrel 112, and occupy substantially the entire cross-sectional area of the syringe barrel 112.

Referring again to FIG. 1, the frame member 152 of the actuating mechanism 150 may be fixedly coupled to the housing 102 via any number of approaches. In some arrangements, the frame member 152 may be formed integrally with the housing 102. The frame member 152 may include a first surface 152a, a second surface 152b, and a threaded opening 152c formed between the first surface 152a and the second surface 152b.

The plunger assembly 160 is moveable along the longitudinal axis L of the syringe barrel 112, and includes a plunger rod 162 having a threaded portion 162a which is threadably coupled to and is disposed within the threaded opening 152c of the frame member 152. The threaded portion 162a of the plunger rod 162, and correspondingly, the threaded opening 152c of the frame member 152 may have a thread pitch suitable for any desired drug delivery rate when driven by the spiral torsion spring 180. The plunger assembly 160 further includes a plunger face 164 that is disposed near the first end 112a of the syringe barrel 112.

The plunger rod guide 170 includes a rod portion 172 that is coupled to the plunger assembly 160 via any number of approaches including, for example, via a splined connection or slotted arrangement that allows for the plunger assembly 160 to be axially displaced relative to the plunger rod guide 170. As such, the plunger rod guide 170 guides rotational and axial movement of the plunger assembly 160.

An inner portion 180a of the spiral torsion spring 180 is coupled to the rod portion 172 of the plunger rod guide 170 via any known approach to exert a force on the plunger rod guide 170 causing the plunger rod guide 170 to rotate about axis L.

Plunger Disclosure

Figure 2:
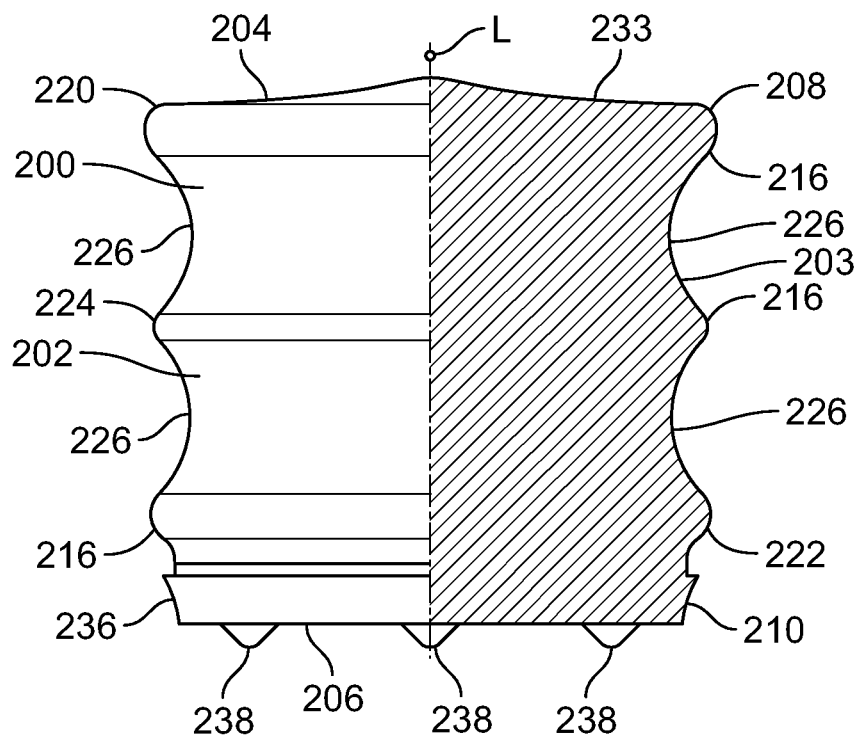
FIG. 2 is a sectional, side elevation detail view of a first embodiment of a plunger for use in the autoinjector device of FIG. 1 in accordance with various embodiments of the present disclosure.
Figure 3:
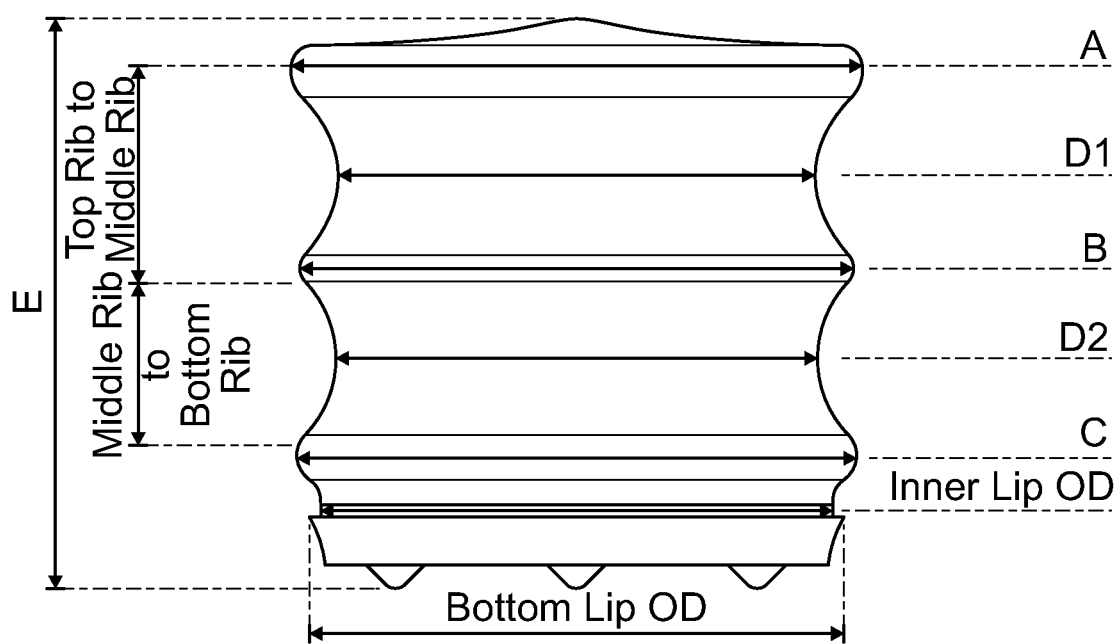
FIG. 3 is a side elevation view of the plunger of FIG. 2 showing dimension labels for Tables 1 and 2 in accordance with various embodiments of the present disclosure.

Example plungers 200 suitable for use in drug delivery devices for the delivery of high viscous products are shown in FIGS. 2 and 3. Each plunger 200 includes a body portion 202 with a generally cylindrical sidewall 203 extending along a longitudinal axis L with leading and trailing surfaces 204, 206 on leading and trailing ends 208, 210 thereof, respectively. The plunger 200 is configured to be engaged on the trailing surface 206 thereof and pushed through the syringe barrel 112 as described with reference to FIG. 1 to thereby expel the medicament 113 from the syringe barrel 112. In preferred embodiments, the body portions 202 described herein are free from cavities, such as to receive a plunger rod therein. So configured, cross-sections of each body portion 202 have unbroken configurations along the axial length thereof between the leading and trailing surfaces 204, 206 thereof.

As shown, the plunger 200 further includes annular ribs 216 that extend radially outwardly from the sidewall 203. The ribs 216 are spaced axially along the body portion 202 and separated by side surfaces 226 that are radially recessed with respect to the ribs 216. The ribs 216 have outer diameters sized to provide contact areas 218 between the plunger 200 and the syringe barrel 112. This decreases the friction magnitude and variability as compared to conventional plungers where all or an extended majority of the sidewall contacts the container. Further, the reduced diameter of the body portion 202 along the side surfaces 226 allows the body portion 203 to compress under axial loads, similar to a bellows, so that the ribs 216 do not significantly expand radially outwardly and the side surfaces 226 do not radially expand past the ribs 216.

In one form, the ribs 216 can be spaced apart from one another more than a travel distance of the plunger 200 resulting from pressure changes during air transport and, in a further form, more than double the travel distance. As such, container closure integrity is maintained during transportation. In one example, a plunger 200 can travel between about 0.7 mm and about 1.12 mm, between about 1.0 mm and about 1.12 mm, and between about 0.7 mm and about 1.0 mm. Accordingly, the distance between the ribs 216 can have corresponding ranges, can have double the corresponding ranges, or be spaced apart more than double the corresponding ranges, such as between about 2 mm and about 4 mm, or between about 2.5 mm and 3.1 mm. In another example, a break loose force of 6N or larger can provide a satisfactory limit on plunger movement during air transport.

In the illustrated forms, the plungers 200 include three annular ribs 216: a leading rib 220, a trailing rib 222, and an intermediate rib 224. It will be understood that for particular uses the plunger 200 can include additional intermediate ribs as desired. The ribs 216 and the sidewall side surfaces 226 extending therebetween can take any suitable form. Moreover, the leading, trailing, and intermediate ribs 220, 222, 224 need not have consistent forms.

In a first form, as shown in FIG. 2, the ribs 216 can have a convexly curved, cross-sectional profile along the longitudinal axis L. Further, the leading and trailing ribs 220, 222 can have a curve with a larger radius than the intermediate rib 224, such that the leading and trailing ribs 220, 220 provide a larger contact area 218 with the container 212 than the intermediate rib 224. If desired, although not shown, each rib 220, 222, 224 can have a curve with a different radius or can each have the same radius. In the form of FIG. 2, the side surfaces 226 of the sidewall 203 extending between the ribs 216 have a concavely curved, cross-sectional profile along the longitudinal axis L FIG. 3 depicts an alternative form of the plunger 200 that includes a body portion 202 with a generally cylindrical sidewall 203 extending along a longitudinal axis L with leading and trailing surfaces 204, 206 on leading and trailing ends 208, 210 thereof, respectively. The plunger 200 is configured to be engaged on the trailing surface 206 thereof and pushed through the syringe barrel 112 as described with reference to FIG. 1 to thereby expel the medicament 113 from the syringe barrel 112.

As shown, the plunger 200 of this form includes annular ribs 216 that extend radially outwardly from the sidewall 203. The ribs 216 are spaced axially along the body portion 202 and separated by side surfaces 226 that are radially recessed with respect to the ribs 216. The ribs 216 have outer diameters sized to provide contact areas 218 between the plunger 200 and the syringe barrel 112. As shown, the plunger 200 can include three ribs 216: a leading rib 220, a trailing rib 222, and an intermediate rib 224. It will be understood that for particular uses the plunger 200 can include additional intermediate ribs as desired. The ribs 216 and the sidewall side surfaces 226 extending therebetween can take any suitable form. As shown in FIG. 3, the plunger 200 can include a rib 216 with a cylindrical portion 228 disposed between convex axial portions 230, as shown in the leading rib 220 thereof. The cylindrical portion 228 provides a larger contact area surface with the container 202 as compared to a curved rib. Further, as shown, the intermediate and trailing ribs 224, 222 of the plunger 200 can have a curved profile with the same radius. Of course, combinations of the ribs 216 shown in FIGS. 2 and 3, as well as other suitable configurations, can also be utilized. In the form of FIG. 3, the side surfaces 226 have a cylindrical middle portion 232 with frustoconical portions 234 having generally concave cross-sections disposed on either axial end thereof to transition between the side surfaces 226 and the adjacent ribs 216.

Figure 24:
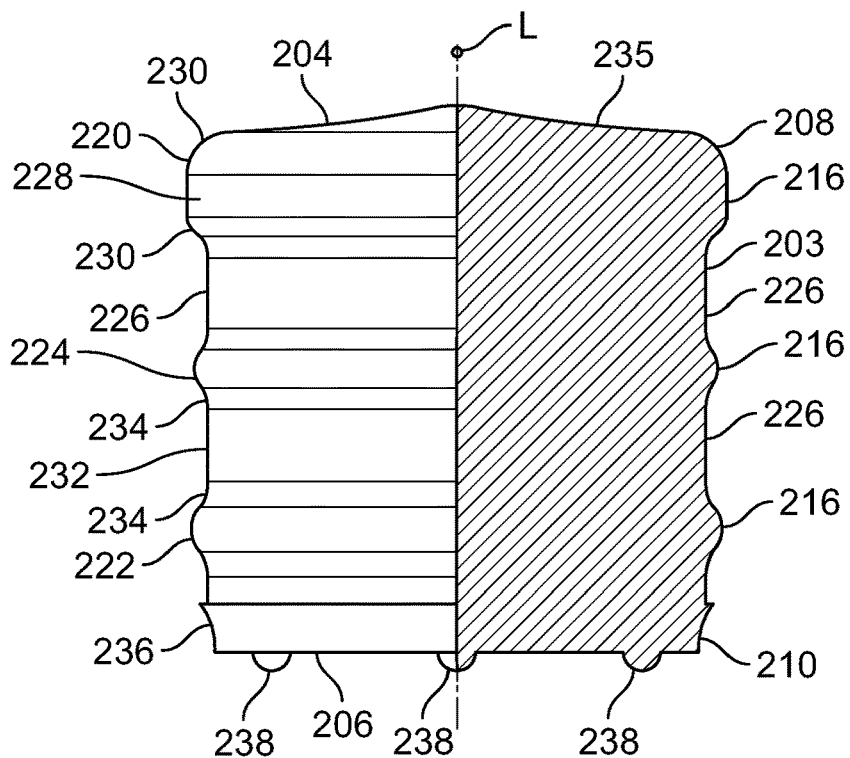
FIG. 24 is a sectional, side elevation detail view of a second embodiment of a plunger for use in the autoinjector device of FIG. 1 in accordance with various embodiments of the present disclosure.

As discussed, the leading surface 204 of the plunger 200 is configured to engage and push the medicament 113 through the syringe barrel 112. As shown in FIGS. 2 and 24, the leading surface 204 can have a pointed configuration to minimize a hold-up volume of the medicament 113 within the syringe barrel 112 by virtue of the leading surface 204 extending into the opening 112e of the syringe barrel 112 and optionally into the needle hub 116/needle 118, described in more detail with reference to FIG. 1.

The configuration of the leading surface 204 can take any desired shape, such as a cone with a concavely curved surface 233 shown in the embodiment of FIG. 2, or a cone with a flat-sided surface 235 shown in the embodiment of FIG. 24. Moreover, the leading surface 204 can have a roughened texture across all or a portion thereof. A roughened texture aids in keeping the plungers 200 from sticking together during processing and storage. In an alternative form, the leading surface 204 can have any suitable material applied thereto to create a roughened texture.

With reference to FIGS. 2 and 24, in some embodiments, the plunger 200 can include a trim edge 236 adjacent to the trailing surface 206 thereof. The trim edge 236 is the result of individual plungers 200 being cut from a common sheet of material when the plungers 200 are formed as a batch. As shown, the trim edge 236 can further have an outer diameter smaller than the outer diameter of the ribs 216, such that the trim edge 236 does not contact the container 212 during use, even while the plunger 200 is under axial load and compressed. Traditionally, the plungers can be cut from the sheet of material so that the trim edge is at the front of the plunger. Moreover, the trim edge 236 can have an outer diameter that engages with the syringe barrel during use. This additional contact area, especially with the uneven nature of cut edges, can add friction magnitude and variability to the drug delivery device during use. Plungers 200 configured as described herein advantageously avoid these problems associated with trim edges.

According to some aspects, the plunger 200 can include one or more protrusions 238 extending away from the trailing surface 206 thereof. The protrusions 238 are preferably disposed around the trailing surface 206 so that the protrusions 238, in combination, provide stable contact for a plunger face 240 pushing the plunger 200 through the container 212. For example, protrusions 238 can also be disposed spaced around the trailing surface 206, such as in an array and/or symmetrically. A protrusion 238 can also be disposed generally centrally on the trailing surface 206. It will be understood that the protrusions 238 can be provided in any suitable shape or configuration, such as conical as in FIG. 2 or dome-shaped in FIG. 3. In the illustrated form, there are four protrusions 238 disposed equally spaced from one another in a circle centered on the trailing surface 206.

The protrusions 238 further advantageously shift the center of mass for plunger 200 rearwardly and can be configured to cushion an initial impact of the plunger face 238 into the plunger 200 during a dispensing action. Moreover, the protrusions 238 also aid in keeping the plungers 200 from sticking together during processing and storage. Accordingly, in combination with the roughened leading surface 204, the curved side surfaces 226, and the ribs 216, the plungers 200 generally do not stick together during bulk processing and storage.

According to one example, the plunger 200 shown in FIGS. 2 and 3 can have the following dimensions: the top rib 200—A—can have a diameter of about 9.4 mm; the middle rib 224—B—can have a diameter of about 9.1 mm; the lower rib 222—C—can have a diameter of about 9.2 mm; the top inner side surface 226—D1—can have a diameter of about 7.9 mm; the lower inner side surface 226—D2—can have a diameter of about 7.9 mm; the total length—E—can be about 9 mm; the top rib 220 to the middle rib 224 can have a distance of about 3.18 mm; the middle rib 224 to the lower rib 222 can have a distance of about 3.08 mm; the bottom lip 236 can have a maximum diameter of about 8.8 mm; and the inner lip can have a diameter of about 8.4 mm. Other example measurements can include: the top 220 and lower rib 222 can have a radius of about 0.5 mm; the middle rib 224 can have a radius of about 0.3 mm; the lower rib 22 to the trailing surface 206 can have a distance of about 1.82 mm; the protrusions 238 can have a radius of about 0.2 mm, a length of about 0.4 mm, and be spaced around a circle having a diameter of about 6.0 mm on the trailing surface 206.

As shown in Tables 1 and 2 below, two sample groups of 2.25 mL plungers were measured. The measurement references in the top row of the Tables are labeled on the plunger 200 of FIG. 3. Histrographs of each measurement shown in Tables 1 and 2 are provided in FIGS. 3-23.

TABLE 1

First Sample Plunger Dimensions

|  | A Top Rib OD | B Middle Rib OD | C Lower Rib OD | D1 Top Inner OD | D2 Lower Inner OD | E Total Length | Top Rib to Middle Rib | Middle Rib to Lower Rib | Bottom Lip OD | Inner Lip OD |
|---|---|---|---|---|---|---|---|---|---|---|
| Ave. (mm) | 9.25 | 8.92 | 9.04 | 7.70 | 7.70 | 8.96 | 3.21 | 3.13 | 8.41 | 8.20 |
| Std. Dev. | 0.02 | 0.02 | 0.02 | 0.02 | 0.02 | 0.02 | 0.05 | 0.04 | 0.03 | 0.05 |

TABLE 2

Second Sample Plunger Dimensions

|  | A Top Rib OD | B Middle Rib OD | C Lower Rib OD | D1 Top Inner OD | D2 Lower Inner OD | E Total Length | Top Rib to Middle Rib | Middle Rib to Lower Rib | Bottom Lip OD | Inner Lip OD |
|---|---|---|---|---|---|---|---|---|---|---|
| Ave. (mm) | 9.45 | 9.11 | 9.23 | 7.89 | 7.89 | 8.97 | 3.20 | 3.14 | 8.51 | 8.26 |
| Std. Dev. | 0.03 | 0.02 | 0.02 | 0.01 | 0.01 | 0.03 | 0.05 | 0.04 | 0.06 | 0.03 |

Figure 25:
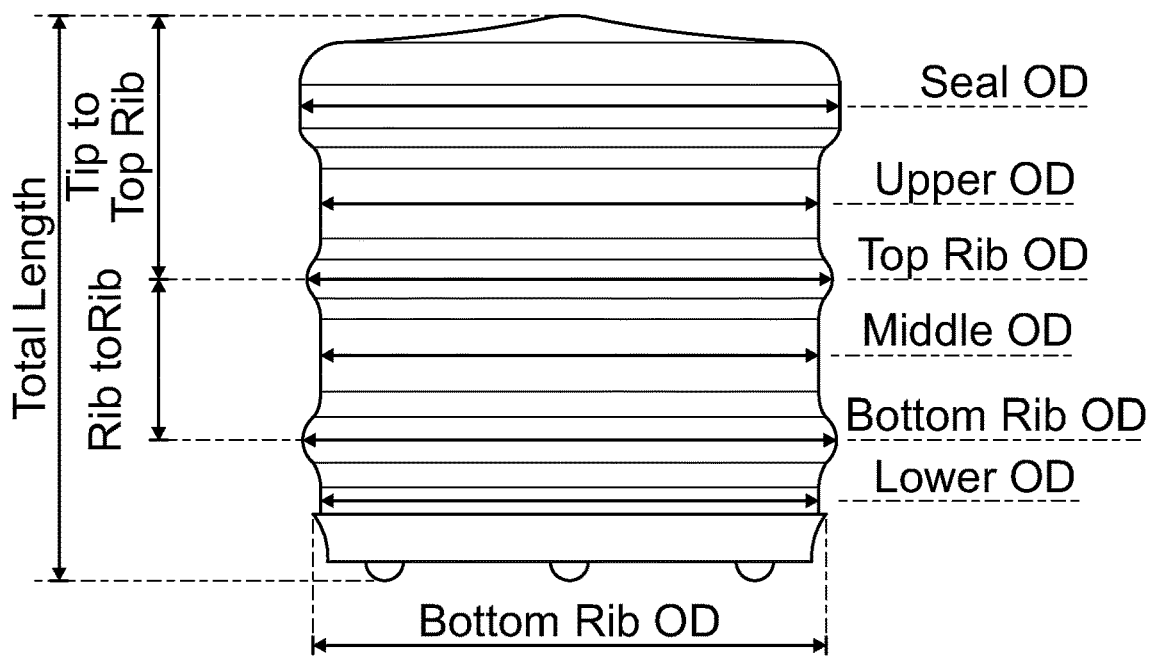
FIG. 25 is a side elevation view of the plunger of FIG. 24 showing dimension labels for Table 3 in accordance with various embodiments of the present disclosure.
Figure 26:
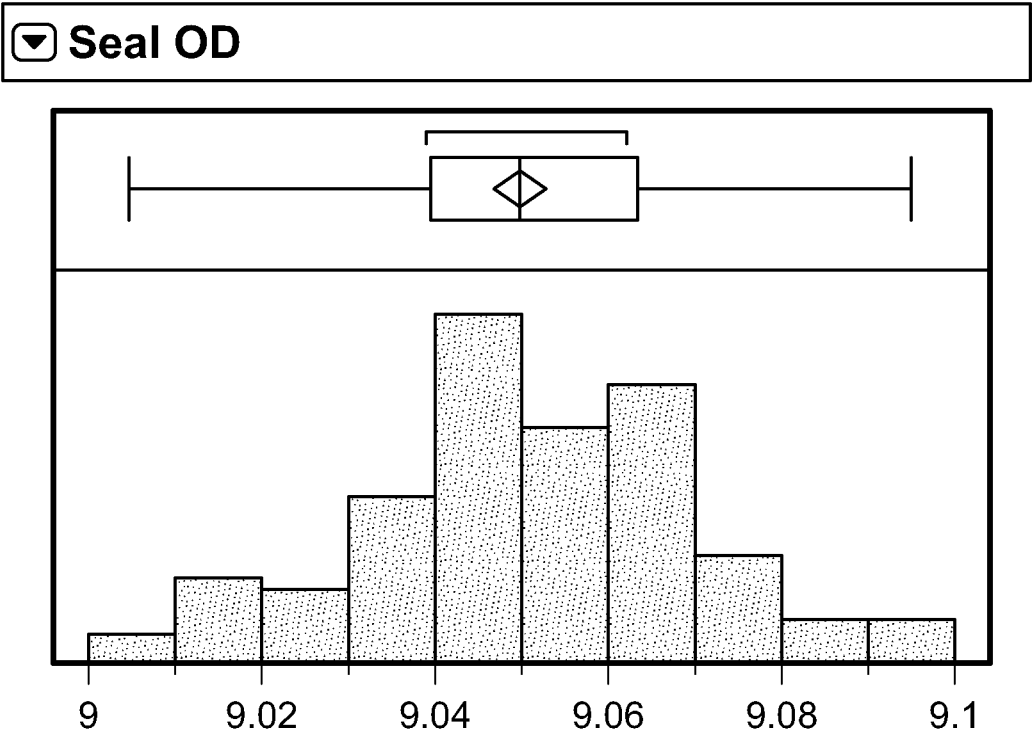
FIG. 26 is a histrograph of a seal diameter measurement of a sample in accordance with various embodiments of the present disclosure.
Figure 27:
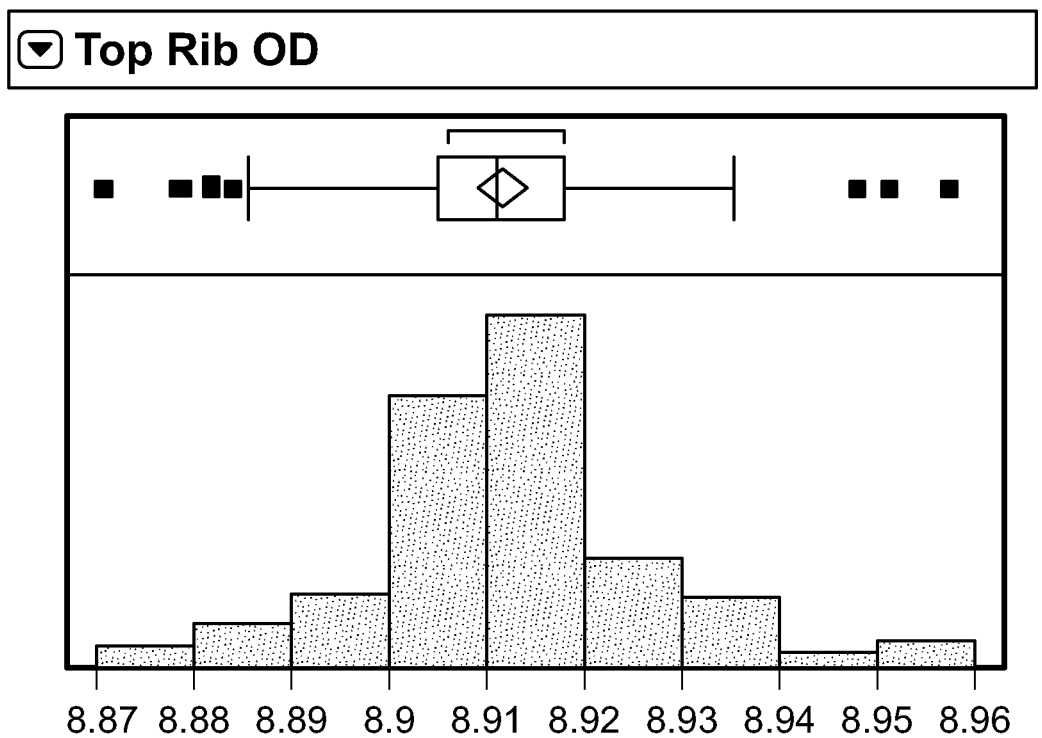
FIG. 27 is a histrograph of a top rib diameter measurement of a sample in accordance with various embodiments of the present disclosure.
Figure 28:
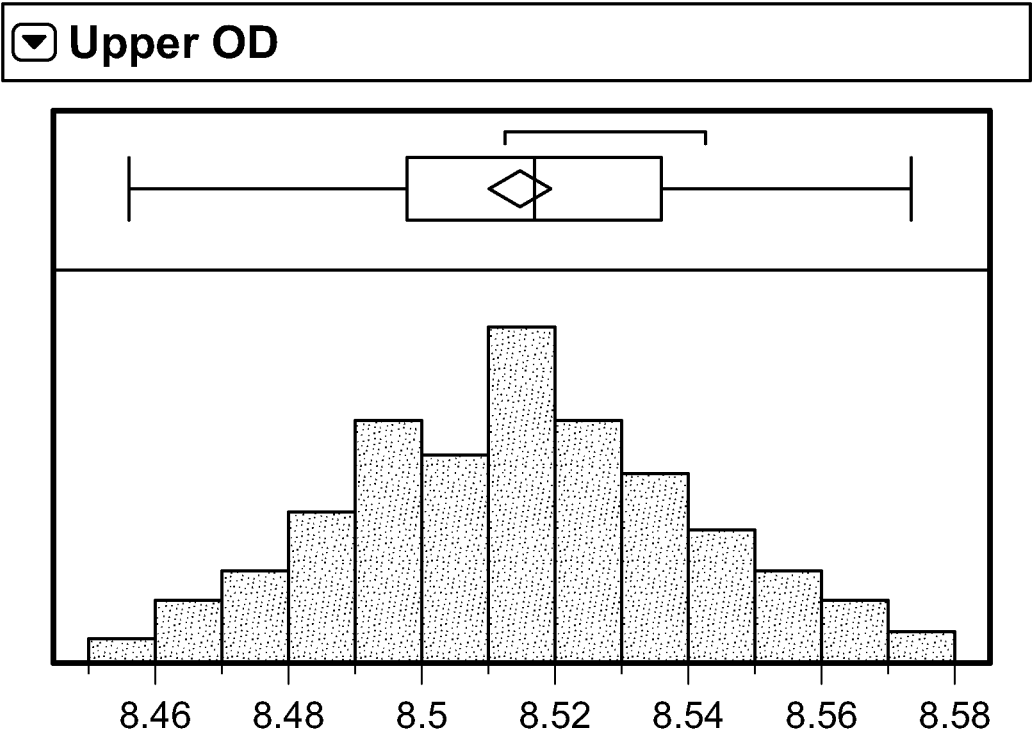
FIG. 28 is a histrograph of an upper diameter measurement of a sample in accordance with various embodiments of the present disclosure.
Figure 29:
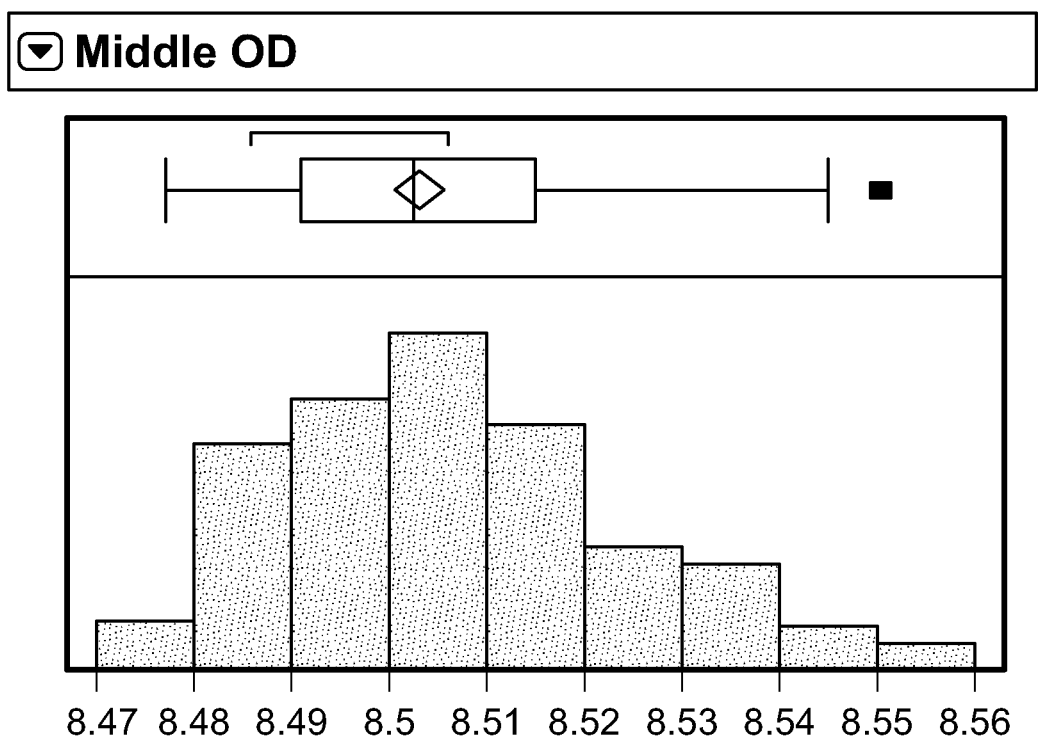
FIG. 29 is a histrograph of a middle diameter measurement of a sample in accordance with various embodiments of the present disclosure.
Figure 30:
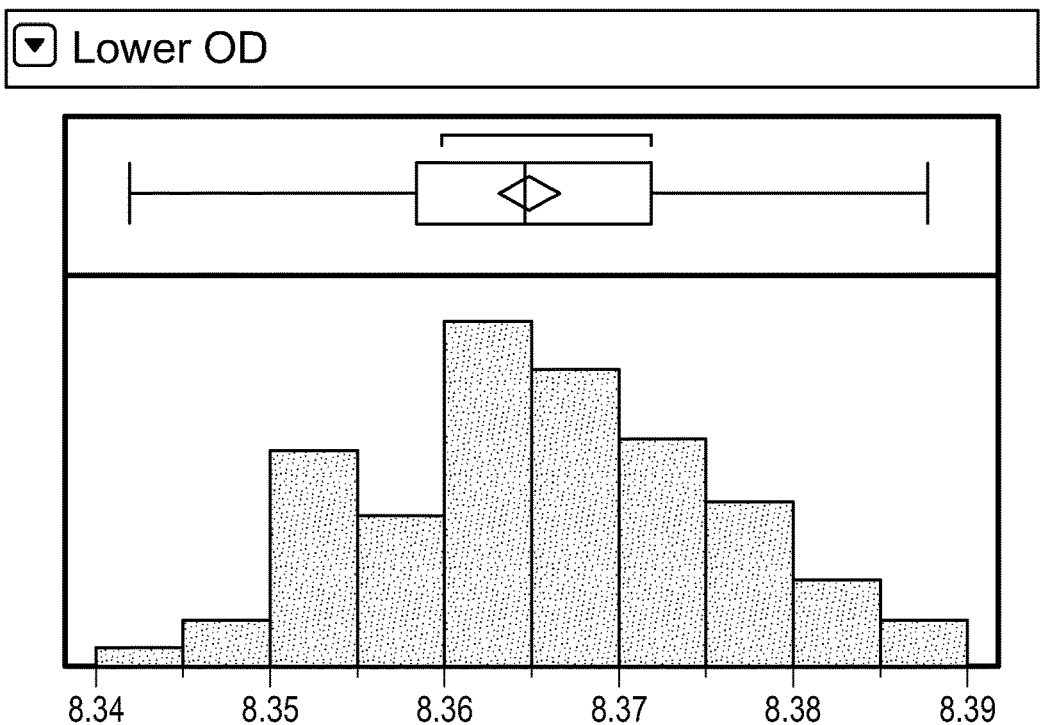
FIG. 30 is a histrograph of a lower diameter measurement of a sample in accordance with various embodiments of the present disclosure.
Figure 31:
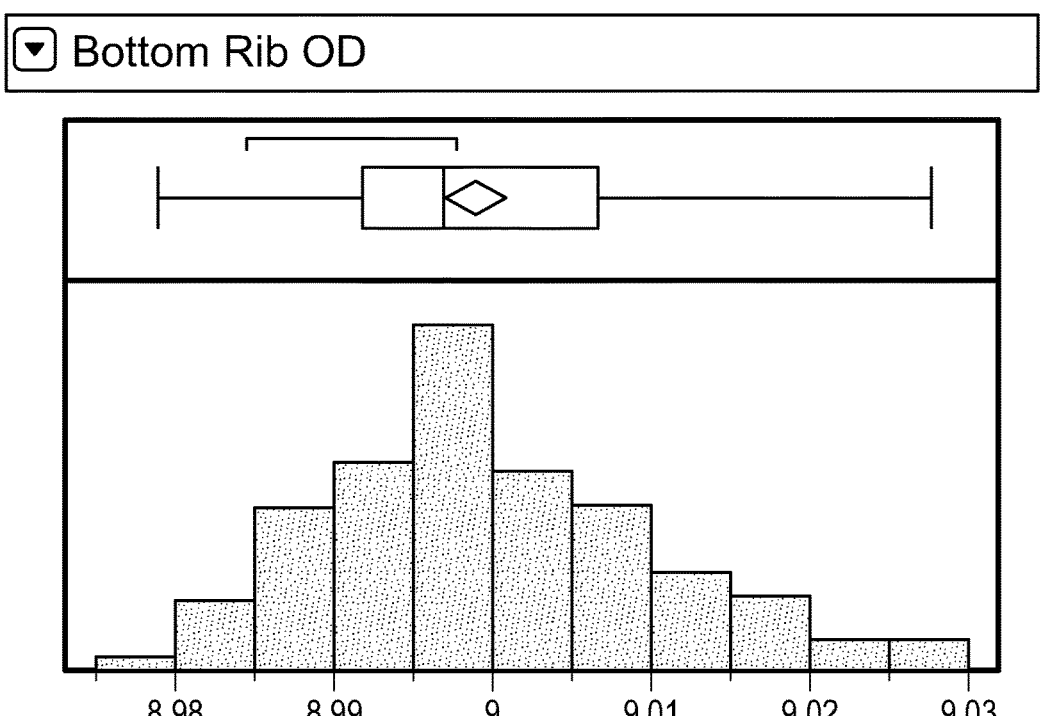
FIG. 31 is a histrograph of a bottom rib diameter measurement of a sample in accordance with various embodiments of the present disclosure.
Figure 32:
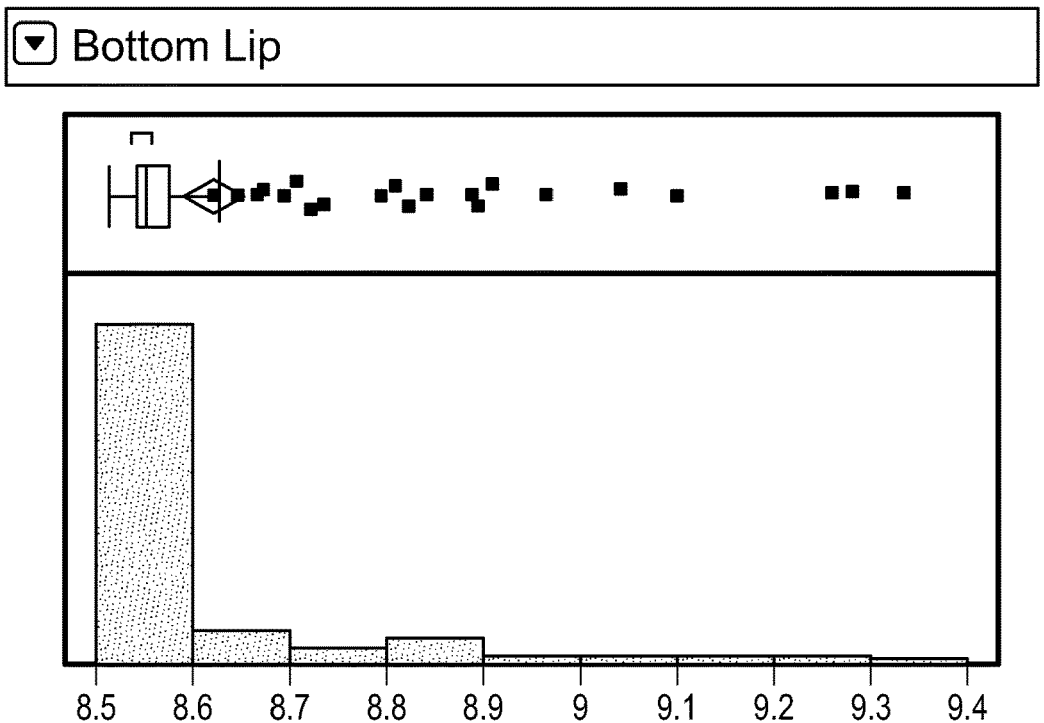
FIG. 32 is a histrograph of a bottom lip diameter measurement of a sample in accordance with various embodiments of the present disclosure.
Figure 33:
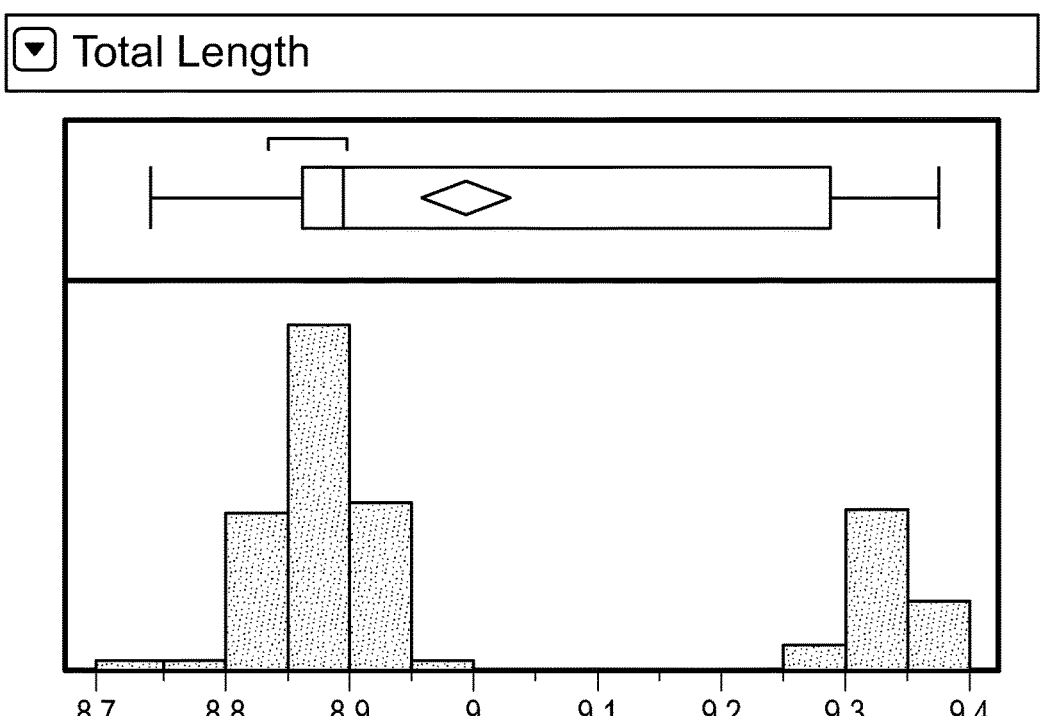
FIG. 33 is a histrograph of a total length measurement of a sample in accordance with various embodiments of the present disclosure.
Figure 34:
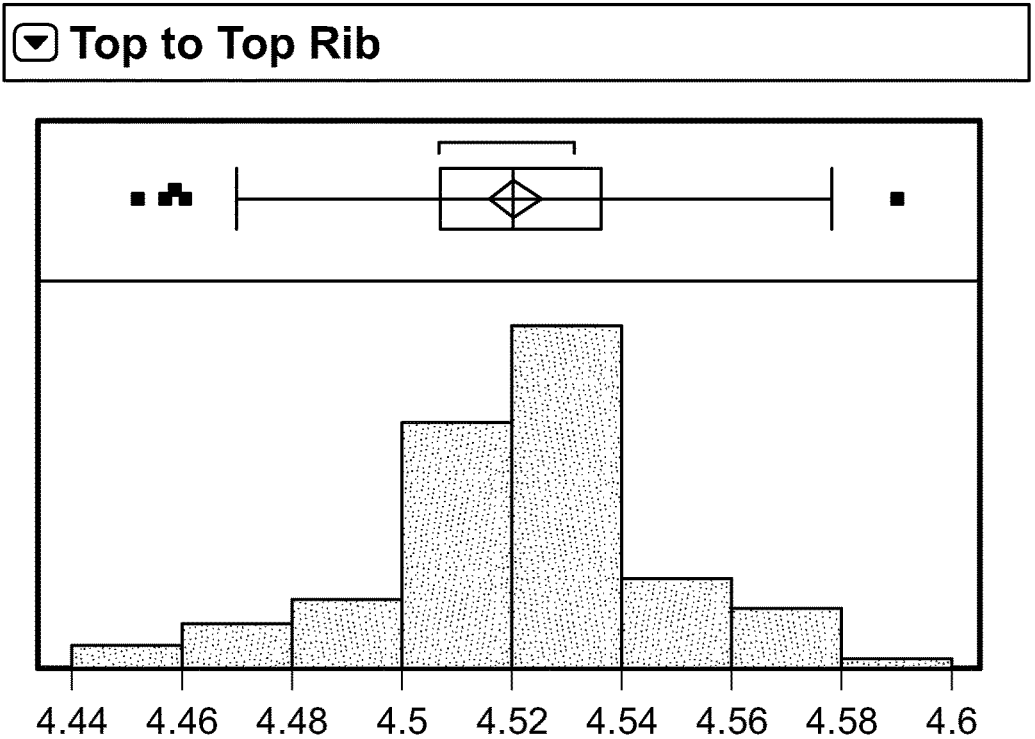
FIG. 34 is a histrograph of a tip to top rib measurement of a sample in accordance with various embodiments of the present disclosure.
Figure 35:
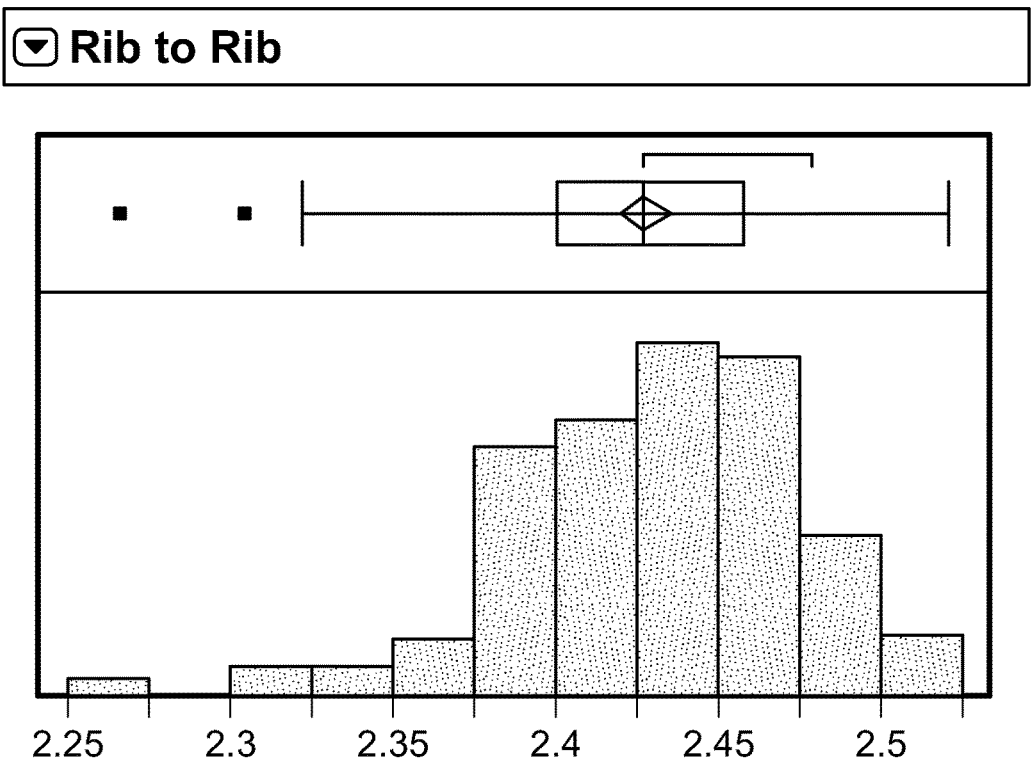
FIG. 35 is a histrograph of a rib to rib measurement of a sample in accordance with various embodiments of the present disclosure.

According to another example, the plunger 200 shown in FIGS. 24 and 25 can have the following dimensions: the seal OD (top rib 220) can have a diameter of about 9.10; the top rib OD (middle rib 224) can have a diameter of about 8.90 mm; the upper OD (side surface 226) can have a diameter 8.50 mm; the middle OD (side surface 226) can have a diameter of about 8.50 mm; the lower OD (adjacent to the trim edge 236) can have a diameter of 8.40 mm; the bottom rib 222 OD can have a diameter of 9.00 mm; the bottom lip (trim edge 236) can have a maximum diameter of 8.70 mm; the total length of the plunger 200 can be about 9.00 mm; the tip to the top (middle rib 224) can have a distance of about 4.40 mm; and the rib to rib (middle 224 to lower 222) can have a distance of about 2.60 mm. Other example measurements can include: the protrusions 238 can have a diameter of about 0.60 mm, a depth of about 0.25 mm, and be spaced around a circle having a diameter of about 6.40 mm on the trailing surface 206; the convex axial portions 230 of the leading rib 220 can have a leading radius of about 0.70 mm and a trailing radius of about 0.60 mm; the cylindrical portion 228 of the leading rib 220 can have a length of about 0.64 mm; the lower rib 222 to the trailing surface 206 can have a distance of about 2.00 mm; and the leading surface 204 can be angled by about 7 degrees with a radius of about 3.00 mm.

As shown in Table 3 below, a sample group of 2.25 mL plungers were measured. The measurement references in the top row of the Table are labeled on the plunger 200 of FIG. 25. Histrographs for each of the measurements shown in Table 3 are shown in FIGS. 26-35.

TABLE 3

Sample Plunger Dimensions

|  | Seal OD | Top Rib OD | Upper OD | Middle OD | Lower OD | Bottom Rib OD | Bottom Lip | Total Length | Tip to Top Rib | Rib to Rib |
|---|---|---|---|---|---|---|---|---|---|---|
| Ave. (mm) | 9.05 | 8.91 | 8.51 | 8.51 | 8.37 | 9.00 | 8.62 | 9.00 | 4.52 | 2.43 |
| Std. Dev. | 0.02 | 0.01 | 0.02 | 0.01 | 0.01 | 0.01 | 0.16 | 0.20 | 0.03 | 0.04 |

With the autoinjector 100 configured with one of the plungers 200, as an axial load is applied to the trailing surface to drive the plunger 200 through the container 212, the plunger 200 is configured to axially compress, similar to a bellows, without significant radial expansion beyond an original diameter of the ribs 216. Significant radial expansion can mean less than 5% of the diameter thereof, less than 3%, less than 2%, and less than 1%. More specifically, the side surfaces 226 of the plunger 200 can be configured to fold and axially compress so that the ribs 216 maintain their radial dimension during use and, thus, provide consistent contact area with the syringe barrel 112 to minimize friction variability. By some approaches, the plunger 200 can be configured to compress between about 10% and about 30% of its length when driven by large axial loads. Typically, the more viscous a product is, the more force is required to dispense the product within a desired dispense time range. The plungers 200 described herein are suitable for use with drugs having a viscosity of up to 100 cP, and more preferably of up to at least 300 cP. Moreover, the plungers 200 are configured to operate as described herein under axial loads of up to at least 500 N.

With regard to container closure integrity, which refers to a container's ability to maintain a sterile barrier against potential contaminants, in a first example with a plunger having a configuration as shown in FIG. 2, the leading rib 220 can maintain container closure integrity with a contact pressure of about 1.2 MPa and the trailing rib 222 can maintain container closure integrity with a contact pressure of about 1.1 MPa. In a second example with a plunger having a configuration as shown in FIG. 24, the leading rib 220 can maintain container closure integrity with a contact pressure of about 0.8 MPa and the trailing rib 222 can maintain container closure integrity with a contact pressure of about 0.9 MPa.

The plungers 200 described herein are particularly suited for use in an autoinjector, described above with reference to FIG. 1. The following data, reflected in the below tables and graphs shown in FIGS. 36-38, utilized an autoinjector device to test plungers configured as shown in FIGS. 2 and 24 with regard to a conventional, threaded plunger.

Figure 36:
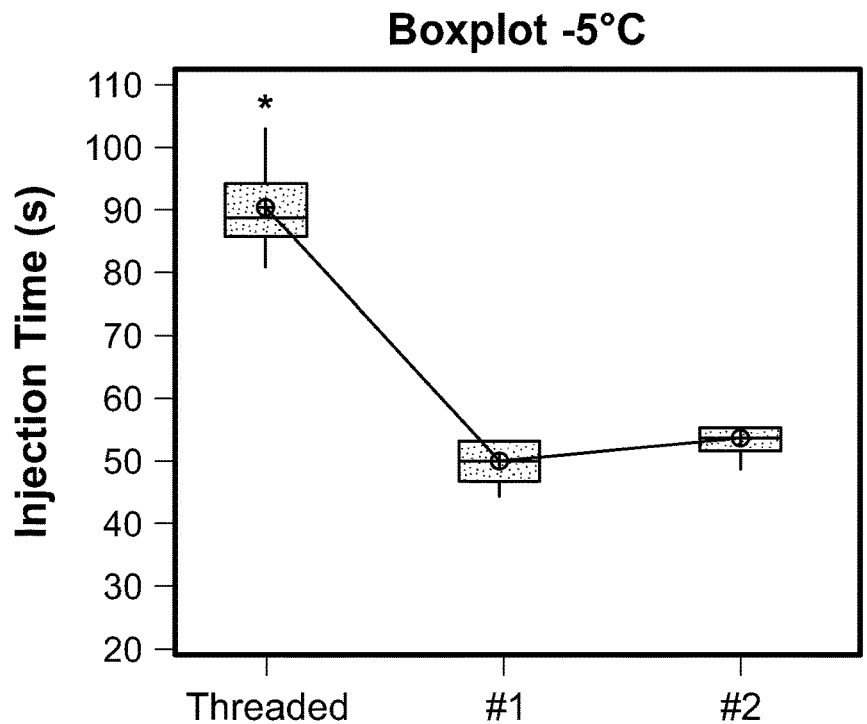
FIG. 36 is a graph showing injection time testing data in accordance with various embodiments of the present disclosure.
Figure 37:
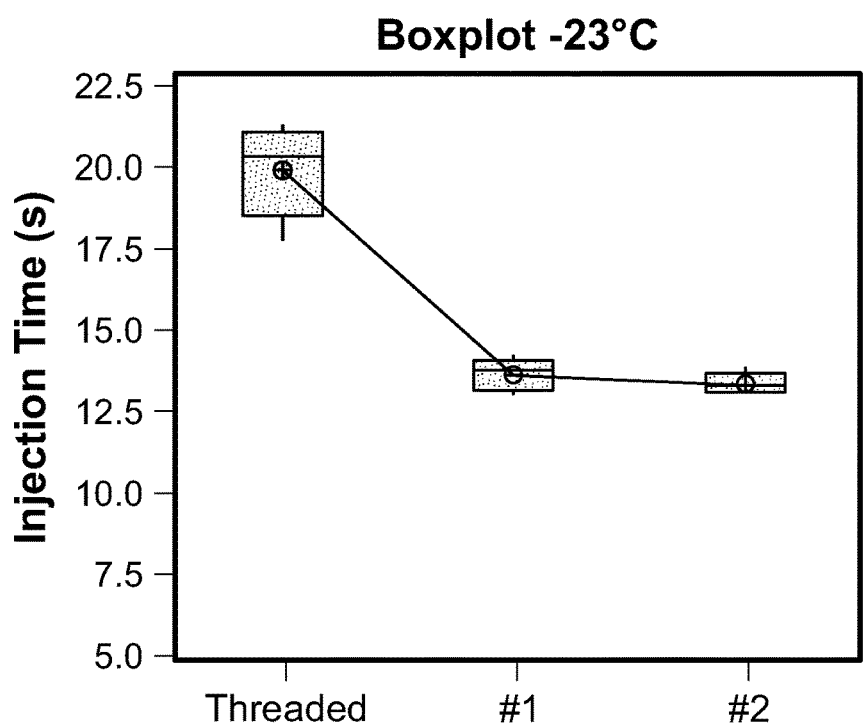
FIG. 37 is another graph showing injection time testing data in accordance with various embodiments of the present disclosure.

As shown in FIGS. 36 and 37, and in Table 4 below, injection time was tested at 5° C. and 23° C. The conventional, threaded plunger provided an average injection time of 90.17 seconds with a standard deviation of 7.10 for 5° C. and an average injection time of 19.00 seconds with a standard deviation of 1.23 for 23° C. The #1 plunger, configured as shown in FIG. 2, provided an average injection time of 49.45 seconds with a standard deviation of 3.63 for 5° C. and an average injection time of 13.65 seconds with a standard deviation of 0.49 for 23° C. Accordingly, the #1 plunger provided a 45% reduction in average and a 49% reduction in standard deviation at 5° C. and a 32% reduction in average and a 60% reduction in standard deviation at 23° C. as compared to the conventional, threaded plunger. The #2 plunger provided a 41% reduction in average and a 60% reduction in standard deviation at 5° C. and a 33% reduction in average and a 73% reduction in standard deviation at 23° C. as compared to the conventional, threaded plunger.

TABLE 4

| Injection Time Testing | | | | |
|---|---|---|---|---|
| | 5° C. | | 23° C. | |
| | Ave. (sec) | Std. Dev. | Ave. (sec) | Std. Dev. |
| Threaded (2345) | 90.17 | 7.10 | 19.99 | 1.23 |
| #1 (FIG. 2) | 49.45 | 3.63 | 13.65 | 0.49 |
| #2 (FIG. 3) | 53.28 | 2.83 | 13.32 | 0.33 |

Figure 38:
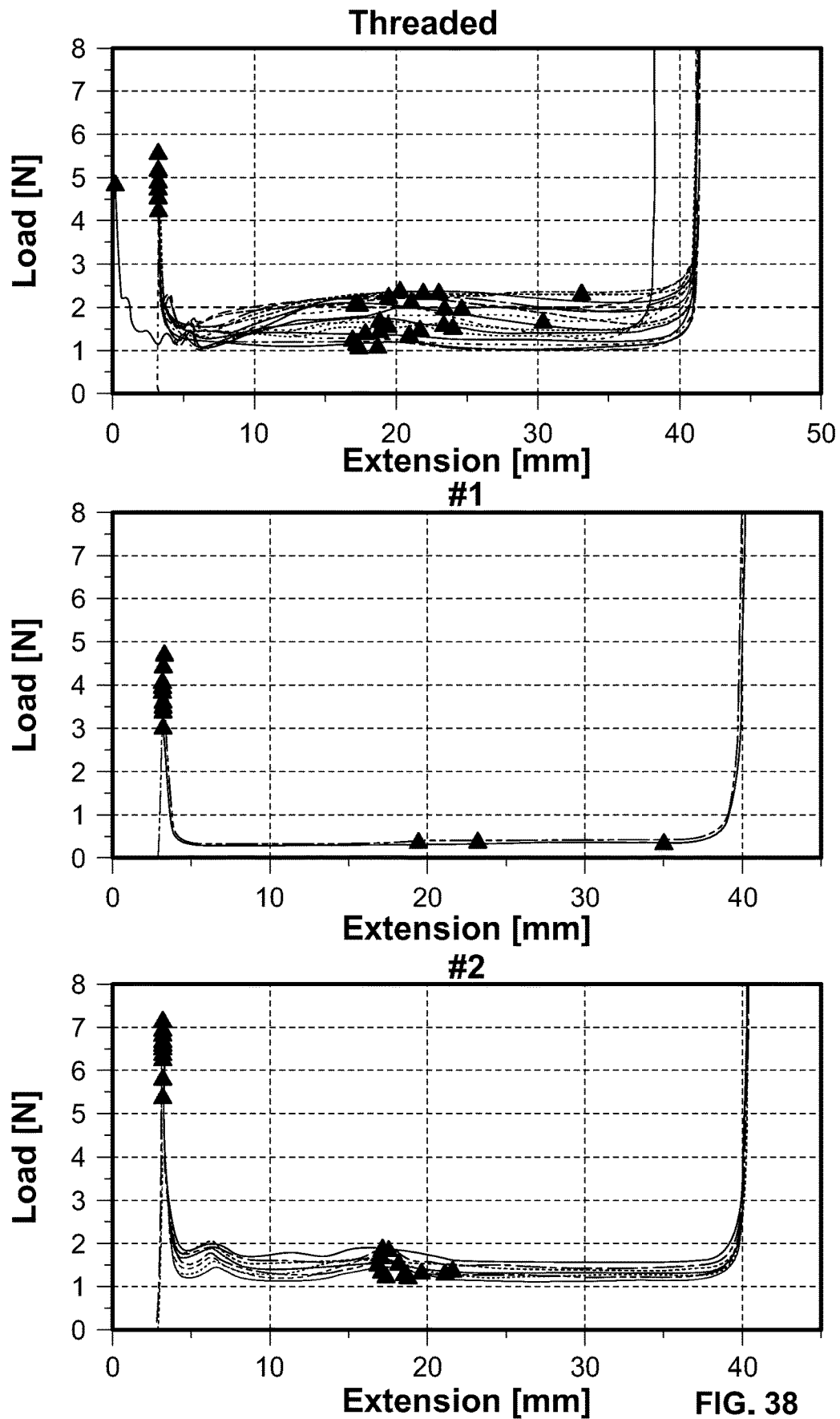
FIG. 38 is a graph showing injection friction force testing data in accordance with various embodiments of the present disclosure.

A conventional, threaded plunger was also tested for mean glide force and standard deviation along with plungers configured as shown in FIG. 2 (#1) and FIG. 24 (#2). FIG. 38 provides graphs showing these test results. As set forth in the below in Table 5, both plungers configured as described herein performed better than the conventional plunger. More specifically, the plunger configured as shown in FIG. 2 had a 77% reduction in mean glide force as compared to the conventional plunger and a 95% reduction in standard deviation. The plunger configured as shown in FIG. 24 had a 17% reduction in mean glide force as compared to the conventional plunger and a 64% reduction in standard deviation.

TABLE 5

| Friction Testing | | |
|---|---|---|
| Plunger (n = 30) | Mean glide force [N] (% reduction from control) Neopak | Std. dev [N] (% reduction from control) Neopak |
| Threaded (2345) | 1.84 | 0.44 |
| #1 (FIG. 2) | 0.42 (77%) | 0.02 (95%) |
| #2 (FIG. 3) | 1.52 (17%) | 0.16 (64%) |

For all tests, a syringe system was prepared with 2.1 ml±0.1 ml media and plunger insertion corresponding to an air gap of at least 2 mm. The plungers were inserted in such a way that media has been in contact with all the surface of the syringe before the plungers are slid down. For tests where break loose "BL" was of importance (friction, break loose and extrusion "BLE", container closure integrity "CCI", and simulated air transport), the syringe-plunger system was preconditioned for 48 hours±3 hours prior to any testing. The 2 days sample conditioning time allows the plunger to set and development an initial BL force.

The BLE force, exerted on the plunger, refers to the force required to expel liquid from the syringe through the staked needle. The BLE test includes closing at two different rates and the BLE force is divided into two parts: Break loose: The initial force needed to initiate the movement of the plunger; and Extrusion: The maximum force reached during the plunger's movement through the syringe, after the effect of break loose are passed. In general, plunger sizes of nominal and +0.2 have friction BL forces in the region or larger than the baseline plunger.

On-Body Injector Disclosure

Figure 39:
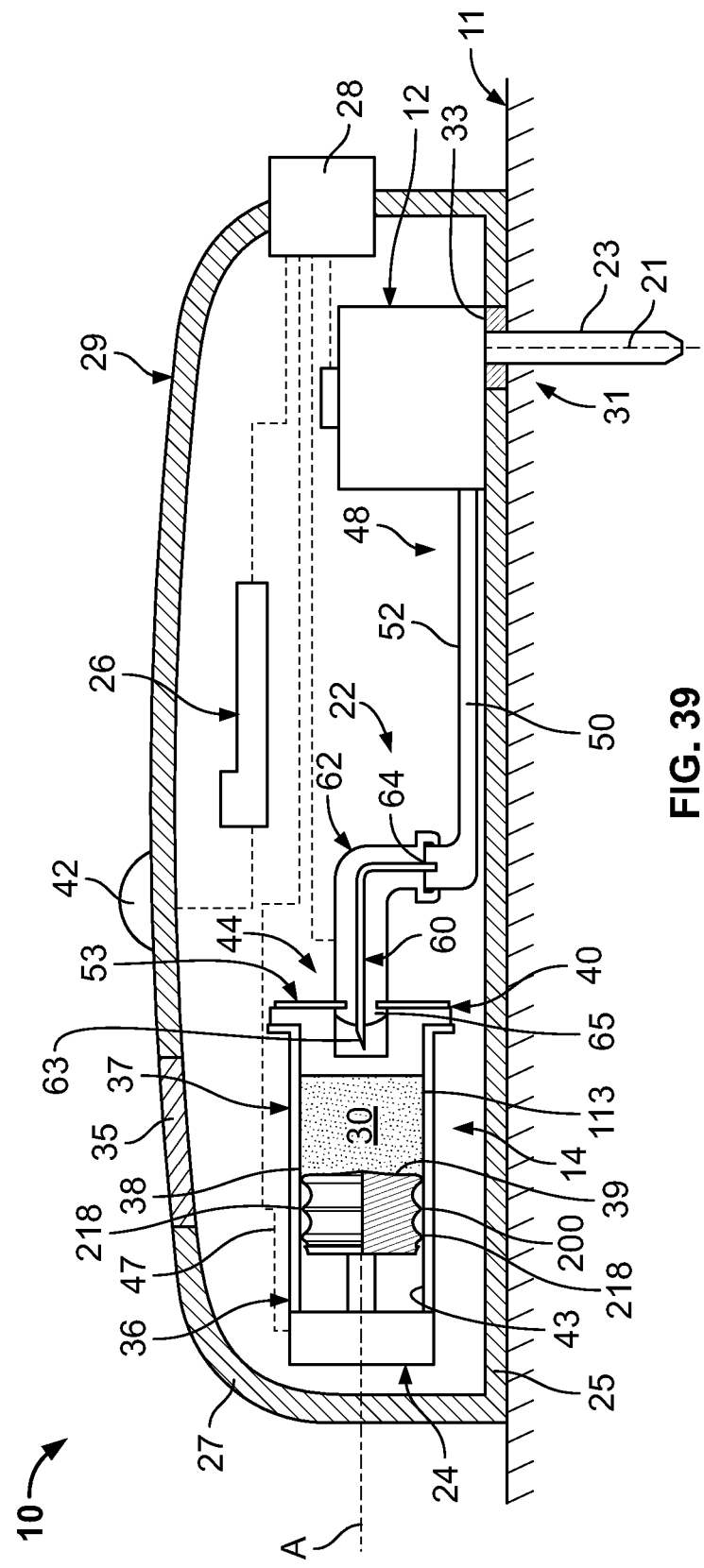
FIG. 39 illustrates a schematic, cross-sectional view of an embodiment of an on-body drug delivery device including a plunger constructed in accordance with various embodiments of the present disclosure.

Although the plungers 200 shown in FIGS. 2 and 24 have been described with reference to being used in an autoinjector drug delivery device 100 discussed above with reference to FIG. 1, the plungers 200 described herein are additionally suitable for use in other drug delivery devices, such as on-body injector devices. FIG. 39 is a schematic illustration of one embodiment of an on-body drug delivery device 10 constructed in accordance with principles of the present disclosure. The drug delivery device 10 may be operated to subcutaneously or transdermally deliver a drug to a patient. In the illustrated embodiment, the drug delivery device 10 is configured as a wearable drug delivery device, such as an on-body injector or an ambulatory infusion pump, and is releasably attachable to the patient's tissue 11 (e.g., the patient's skin). In other embodiments (not illustrated), the drug delivery device 10 may be configured as a pen-type injector, such as an autoinjector or injection pen, which is temporarily held against the patient's tissue 11 over the course of the injection. The drug delivery device 10 may be configured to automatically deliver a fixed or a patient/operator-settable dose of the drug over a controlled or selected period of time. Furthermore, the drug delivery device 10 may be intended for self-administration by the patient, or may be operated by a formally trained healthcare professional or other caregiver to administer the injection.

Generally, the drug delivery device 10 may include an insertion mechanism 12, a container 14, a fluid pathway assembly 22, a drive mechanism 24, and a controller 26, each of which may be disposed within an interior space of a main housing 29. An actuator 28 (e.g., a user-depressible button, touchscreen, microphone, etc.) may protrude through or otherwise be disposed at an exterior surface of the housing 29 and may be configured to initiate operation of the drug delivery device 10 by activating, via mechanical and/or electrical means (shown in dotted lines in FIG. 39), the insertion mechanism 12, the fluid pathway assembly 22, the drive mechanism 24, the controller 26, and/or other mechanisms and/or electronics. In embodiments where the actuator 28 is a button that is depressed or otherwise physically moved by a user or patient, the actuator 28 may be configured to exert a motive force needed to activate the insertion mechanism 12, the fluid pathway assembly 22, the drive assembly 24, the controller 26, and/or other mechanisms. In such embodiments, the actuator 28 may be physically connected to, either directly or indirectly via a mechanical linkage, the insertion mechanism 12, the drive mechanism 24, the fluid pathway assembly 22, and/or other mechanisms such that manually depressing or otherwise interacting with the actuator 28 supplies the motive force necessary to activate the insertion mechanism 12, the drive mechanism 24, the fluid pathway assembly 22, and/or other mechanisms. For example, in some embodiments, manually depressing the actuator 28 may cause the fluid pathway assembly 22 to move towards the stationary container 14, or cause the container 14 to move towards the stationary fluid pathway assembly 22, and thereby cause a container access needle to penetrate through a seal member into a reservoir or interior volume of the container 14. Additionally or alternatively, the actuator 28 may operate as an input device that transmits an electrical and/or mechanical signal to the controller 26, which in turn may execute programmable instructions to control operation of the insertion mechanism 12, the drive mechanism 24, the fluid pathway assembly 22, and/or other mechanisms. In such embodiments, the controller 26 may include a processor (e.g., a microprocessor) and a non-transitory memory for storing the programmable instructions to be executed by the processor. Furthermore, in such embodiments, the drug delivery device 10 may include an internal actuator (e.g., an electric motor, a pneumatic or hydraulic pump, and/or a source of pressurized gas or liquid) which is separate from the actuator 28 and which, in response to an electrical control signal received from the controller 26, exerts the motive force needed to activate the insertion mechanism 12, the drive mechanism 24, the fluid pathway assembly 22, and/or other mechanisms.

Still referring to FIG. 39, the housing 29 may include a bottom wall 25 configured to be releasably attached (e.g., adhered with an adhesive) to the patient's tissue 11, and a top wall 27 including one or more visual indicators 42 (e.g., lights, graphical displays, etc.) and/or a window 35 for viewing the container 14 and a medicament 113 contained therein. The one or more visual indicators 42 may be used to communicate information to the user about the operational state of the drug delivery device 10 and/or the condition of the medicament 113. An opening 31 may be formed in the bottom wall 25, and optionally a pierceable sterile barrier 33, such as a pierceable septum, may extend across the opening 31 to seal the interior of the housing 29 prior to use. In some embodiments, the pierceable sterile barrier 33 may be omitted, and instead a removable sealing member (not illustrated) may cover and seal close the opening 31 prior to use.

After the bottom wall 25 of the housing 29 is attached to the patient's tissue 13, the insertion mechanism 12 may be activated to move a delivery member from a retracted position within the housing 29 to a deployed position extending outside of the housing 29. In the present embodiment, this may include the insertion mechanism 12 inserting a needle or trocar 21 and a hollow cannula 23 surrounding the trocar 21 through the pierceable sterile barrier 33 and into the patient's tissue 11, as illustrated in FIG. 39. Immediately or shortly thereafter, the insertion mechanism 12 may automatically retract the needle 21, leaving the distal open end of the cannula 23 inside the patient for subcutaneous delivery of the medicament 113. The needle 21 may be solid and have a sharpened end for piercing the patient's skin 11. Furthermore, the needle 21 may be made of a material that is more rigid than the cannula 23. In some embodiments, the needle 21 may be made of metal, whereas the cannula 23 may be made of plastic or another polymer. The relative flexibility of the cannula 23 may allow it to be disposed subcutaneously within the patient's tissue 11 for a period of a time without causing pain or significant discomfort to the patient.

In some embodiments, the insertion mechanism 12 may include one or more springs (e.g., coil springs, torsion springs, etc.) initially retained in an energized state, and which are released upon depression of the actuator 28 in order to insert the needle 21 and cannula 23, or hollow needle, into the patient. Furthermore, retraction of the needle 21 may be achieved by the automatic release of another spring after the needle 21 and cannula 23 have been inserted into the patient. Other power sources for insertion and/or retraction are possible, including, for example, an electric motor, a hydraulic or pneumatic pump, or a canister that releases a pressurized gas or pressurized liquid to provide actuation energy.

The container 14, which in some contexts may be referred to as a primary container, may include a wall 38 with an interior surface 43 defining a reservoir 30 that is filled with the medicament 113 and an exterior surface 47. In some embodiments, the reservoir 30 may be pre-filled with the medicament 113 by a drug manufacturer prior to installation of the container 14 in the drug delivery device 10. In some embodiments, the container 14 may be rigidly connected to the housing 29 such that the container 14 cannot move relative to the housing; whereas, in other embodiments, the container 14 may be slidably connected to the housing 29 such that the container 14 can move relative to the housing 29 during operation of the drug delivery device 10. The container 14 may have an elongate, barrel-like or cylindrical shape extending along a longitudinal axis A. In embodiments where the drug delivery device 10 is configured as an on-body injector, the longitudinal axis A of the container 14 may be perpendicular or substantially perpendicular, or otherwise non-parallel, to a direction in which the insertion mechanism 12 inserts a delivery member such as the cannula 23 into the patient. This configuration may allow the on-body injector to have a generally planar, low-profile shape that can be worn by the patient without impeding the patient's movement. Initially, the plunger 200 may be positioned in the reservoir 30 at a proximal end 36 of the container 14. The plunger 200 may sealingly and slidably engage the interior surface 43 of the wall 38 of the container 14, and may be movable relative to the wall 38 of the container 14.

The volume of the medicament 113 contained in the reservoir 30 prior to delivery may be: any volume in a range between approximately (e.g., ±10%) 0.5-20 mL, or any volume in a range between approximately (e.g., ±10%) 0.5-10 mL, or any volume in a range between approximately (e.g., ±10%) 1-10 mL, or any volume in a range between approximately (e.g., ±10%) 1-8 mL, or any volume in a range between approximately (e.g., ±10%) 1-5 mL, or any volume in a range between approximately (e.g., ±10%) 1-3.5 mL, or any volume in a range between approximately (e.g., ±10%) 1-3 mL, or any volume in a range between approximately (e.g., ±10%) 1-2.5 mL, or any volume in a range between approximately (e.g., ±10%) 1-2 mL, or any volume equal to or less than approximately (e.g., ±10%) 4 mL, or any volume equal to or less than approximately (e.g., ±10%) 3.5 mL, or any volume equal to or less than approximately (e.g., ±10%) 3 mL, or any volume equal to or less than approximately (e.g., ±10%) 2.5 mL, or any volume equal to or less than approximately (e.g., ±10%) 2 mL, or any volume equal to or less than approximately (e.g., ±10%) 1.5 mL, or any volume equal to or less than approximately (e.g., ±10%) 1 mL. The reservoir 30 may be completely or partially filled with the medicament 113. The medicament 113 may be one or more of the drugs described below, such as, for example, a granulocyte colony-stimulating factor (G-CSF), a PCSK9 (Proprotein Convertase Subtilisin/Kexin Type 9) specific antibody, a sclerostin antibody, or a calcitonin gene-related peptide (CGRP) antibody.

During operation of the drug delivery device 10, the drive mechanism 24 may push the plunger 200 along the longitudinal axis A from the proximal end 36 of the container 14 to a distal end 37 of the container 14 in order to expel the medicament 113 from the container 14. In some embodiments, the drive mechanism 24 may include one or more springs (e.g., coil springs, torsion springs, etc.) initially retained in an energized state, and which are released upon depression of the actuator 28. Following their release, the spring(s) may expand or contract to move the plunger 200 through the reservoir 30 along the longitudinal axis A from the proximal end 36 of the container 14 to the distal end 37 of the container 14. In other embodiments, the drive mechanism 24 may include an electric motor (not illustrated) which rotates a gear mechanism, including for example one or more sprocket gears, to cause axial motion of the plunger 200 through the reservoir 30. In still further embodiments, the drive mechanism 24 may include both an electric motor and spring(s), wherein the electric motor regulates expansion of the spring(s) via a tether or pulley system. In still further embodiments, the drive mechanism 24 may include a canister that releases a pressurized gas or pressurized liquid to provide actuation energy. Other examples are possible.

The fluid pathway assembly 22 may be configured to establish fluid communication between the container 14 and the insertion mechanism 12 via a sterile fluid flow path during operation of the drug delivery device 10. The first end 44 of the fluid pathway assembly 22 may include the container access needle 60 and an overmold member 62. In general, the overmold member 62 may serve as a mounting member or connection hub for the container access needle 60 and provide a portion of the container access needle 60 which does not access the reservoir 30 with an enlarged outer dimension, such as an enlarged outer diameter. The container access needle 60 may have a sharpened end or point 63, corresponding to a proximal end of the container access needle 60, and a distal end 64 in fluid communication with the fluid passage 50.

The fluid pathway assembly 22 may include a first end 44 connected to the container 14, a second end 48 connected to the insertion mechanism 12, and a fluid passage 50 extending between the first end 44 and the second end 48. As described in more detail below, in some embodiments the first end 44 of the fluid pathway assembly 22 may be connected to the container 14 via a clip member 53. The fluid passage 50 may be sterilized, and may be partially or entirely made of a flexible tubing 52. Initially, there may be slack in the flexible tubing 52 to allow the fluid pathway assembly 22 to move relative to the housing 29 and/or to allow components of the insertion mechanism 12 to which the fluid pathway assembly 22 is attached to move relative to the housing 29.

Drug Disclosure

The above description describes various assemblies, devices, and methods for use with a drug delivery device. It should be clear that the system, drug delivery device, or methods can further comprise use of a medicament listed below with the caveat that the following list should neither be considered to be all inclusive nor limiting. The medicament will be contained in a chamber or reservoir. In some instances, the reservoir is a primary container that is either filled or pre-filled for treatment with the medicament. The primary container can be a cartridge or a pre-filled syringe.

For example, the drug delivery device or more specifically the reservoir of the device may be filled with colony stimulating factors, such as granulocyte colony-stimulating factor (G-CSF). Such G-CSF agents include, but are not limited to, Neupogen® (filgrastim) and Neulasta® (pegfilgrastim). In various other embodiments, the drug delivery device may be used with various pharmaceutical products, such as an erythropoiesis stimulating agent (ESA), which may be in a liquid or a lyophilized form. An ESA is any molecule that stimulates erythropoiesis, such as Epogen® (epoetin alfa), Aranesp® (darbepoetin alfa), Dynepo® (epoetin delta), Mircera® (methyoxy polyethylene glycol-epoetin beta), Hematide®, MRK-2578, INS-22, Retacrit® (epoetin zeta), Neorecormon® (epoetin beta), Silapo® (epoetin zeta), Binocrit® (epoetin alfa), epoetin alfa Hexal, Abseamed® (epoetin alfa), Ratioepo® (epoetin theta), Eporatio® (epoetin theta), Biopoin® (epoetin theta), epoetin alfa, epoetin beta, epoetin zeta, epoetin theta, and epoetin delta, as well as the molecules or variants or analogs thereof as disclosed in the following patents or patent applications, each of which is herein incorporated by reference in its entirety: U.S. Pat. Nos. 4,703,008; 5,441,868; 5,547,933; 5,618,698; 5,621,080; 5,756,349; 5,767,078; 5,773,569; 5,955,422; 5,986,047; 6,583,272; 7,084,245; and 7,271,689; and PCT Publication Nos. WO 91/05867; WO 95/05465; WO 96/40772; WO 00/24893; WO 01/81405; and WO 2007/136752.

An ESA can be an erythropoiesis stimulating protein. As used herein, "erythropoiesis stimulating protein" means any protein that directly or indirectly causes activation of the erythropoietin receptor, for example, by binding to and causing dimerization of the receptor. Erythropoiesis stimulating proteins include erythropoietin and variants, analogs, or derivatives thereof that bind to and activate erythropoietin receptor; antibodies that bind to erythropoietin receptor and activate the receptor; or peptides that bind to and activate erythropoietin receptor. Erythropoiesis stimulating proteins include, but are not limited to, epoetin alfa, epoetin beta, epoetin delta, epoetin omega, epoetin iota, epoetin zeta, and analogs thereof, pegylated erythropoietin, carbamylated erythropoietin, mimetic peptides (including EMP1/hematide), and mimetic antibodies. Exemplary erythropoiesis stimulating proteins include erythropoietin, darbepoetin, erythropoietin agonist variants, and peptides or antibodies that bind and activate erythropoietin receptor (and include compounds reported in U.S. Publication Nos. 2003/0215444 and 2006/0040858, the disclosures of each of which is incorporated herein by reference in its entirety) as well as erythropoietin molecules or variants or analogs thereof as disclosed in the following patents or patent applications, which are each herein incorporated by reference in its entirety: U.S. Pat. Nos. 4,703,008; 5,441,868; 5,547,933; 5,618,698; 5,621,080; 5,756,349; 5,767,078; 5,773,569; 5,955,422; 5,830,851; 5,856,298; 5,986,047; 6,030,086; 6,310,078; 6,391,633; 6,583,272; 6,586,398; 6,900,292; 6,750,369; 7,030,226; 7,084,245; and 7,217,689; U.S. Publication Nos. 2002/0155998; 2003/0077753; 2003/0082749; 2003/0143202; 2004/0009902; 2004/0071694; 2004/0091961; 2004/0143857; 2004/0157293; 2004/0175379; 2004/0175824; 2004/0229318; 2004/0248815; 2004/0266690; 2005/0019914; 2005/0026834; 2005/0096461; 2005/0107297; 2005/0107591; 2005/0124045; 2005/0124564; 2005/0137329; 2005/0142642; 2005/0143292; 2005/0153879; 2005/0158822; 2005/0158832; 2005/0170457; 2005/0181359; 2005/0181482; 2005/0192211; 2005/0202538; 2005/0227289; 2005/0244409; 2006/0088906; and 2006/0111279; and PCT Publication Nos. WO 91/05867; WO 95/05465; WO 99/66054; WO 00/24893; WO 01/81405; WO 00/61637; WO 01/36489; WO 02/014356; WO 02/19963; WO 02/20034; WO 02/49673; WO 02/085940; WO 03/029291; WO 2003/055526; WO 2003/084477; WO 2003/094858; WO 2004/002417; WO 2004/002424; WO 2004/009627; WO 2004/024761; WO 2004/033651; WO 2004/035603; WO 2004/043382; WO 2004/101600; WO 2004/101606; WO 2004/101611; WO 2004/106373; WO 2004/018667; WO 2005/001025; WO 2005/001136; WO 2005/021579; WO 2005/025606; WO 2005/032460; WO 2005/051327; WO 2005/063808; WO 2005/063809; WO 2005/070451; WO 2005/081687; WO 2005/084711; WO 2005/103076; WO 2005/100403; WO 2005/092369; WO 2006/50959; WO 2006/02646; and WO 2006/29094.

Examples of other pharmaceutical products for use with the device may include, but are not limited to, antibodies such as Vectibix® (panitumumab), Xgeva™ (denosumab) and Prolia™ (denosamab); other biological agents such as Enbrel® (etanercept, TNF-receptor/Fc fusion protein, TNF blocker), Neulasta® (pegfilgrastim, pegylated filgrastim, pegylated G-CSF, pegylated hu-Met-G-CSF), Neupogen® (filgrastim, G-CSF, hu-MetG-CSF), and Nplate® (romiplostim); small molecule drugs such as Sensipar® (cinacalcet). The device may also be used with a therapeutic antibody, a polypeptide, a protein or other chemical, such as an iron, for example, ferumoxytol, iron dextrans, ferric glyconate, and iron sucrose. The pharmaceutical product may be in liquid form, or reconstituted from lyophilized form.

Figure 4:
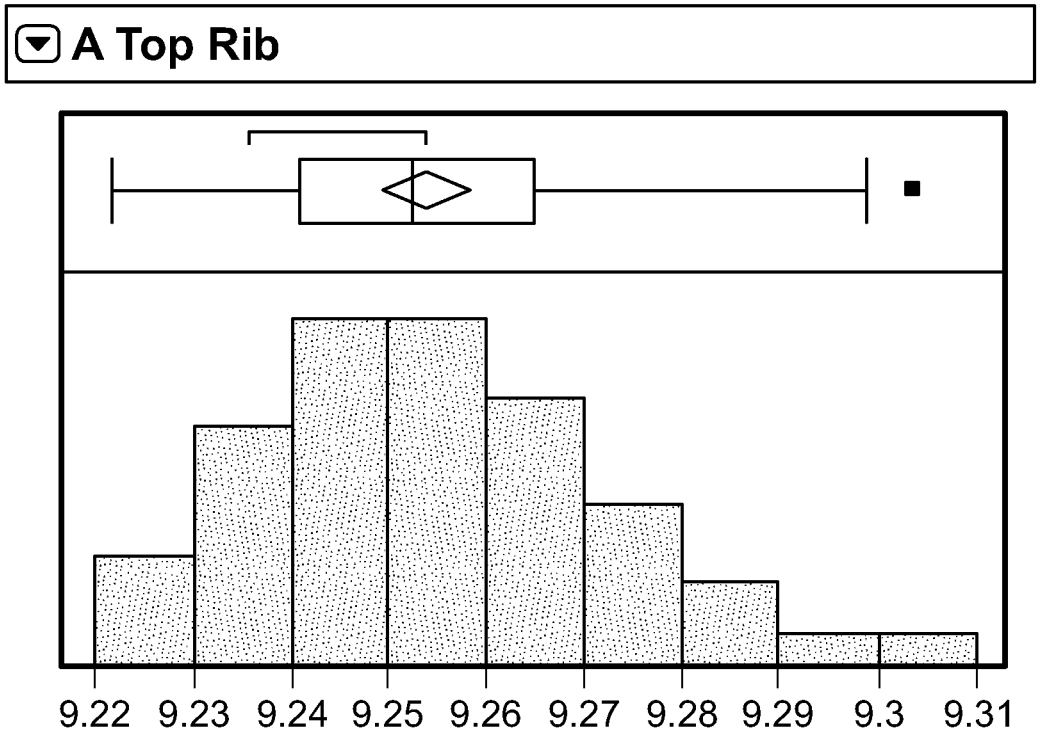
FIG. 4 is a histrograph of a top rib diameter measurement of a first sample in accordance with various embodiments of the present disclosure.
Figure 5:
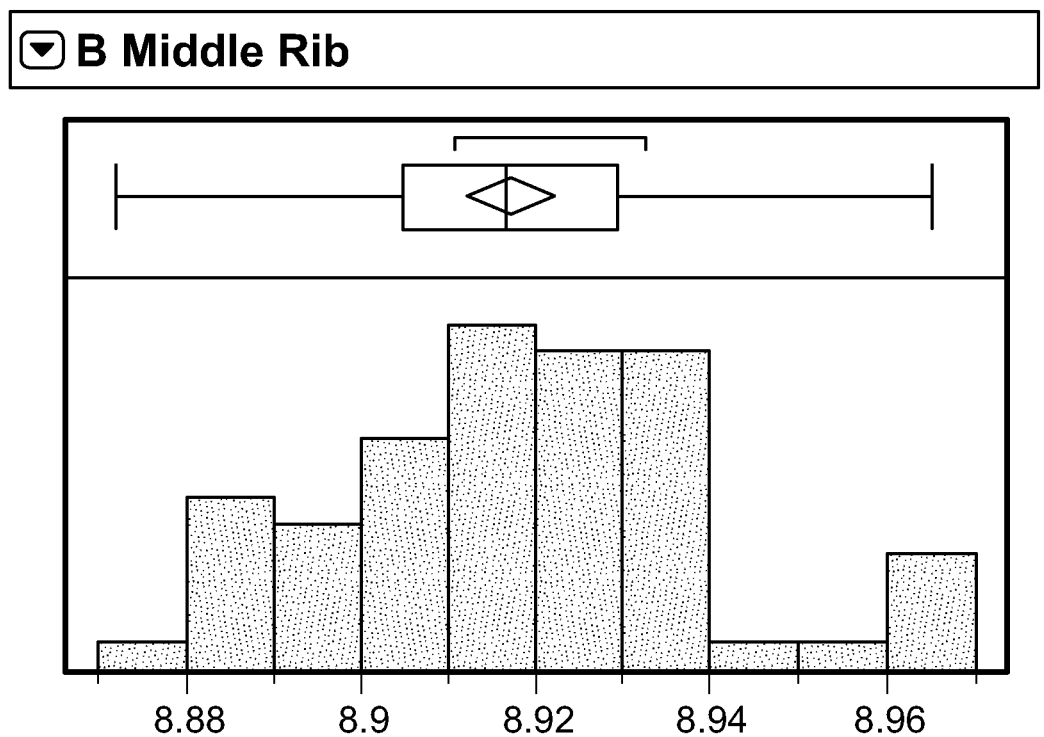
FIG. 5 is a histrograph of a middle rib diameter measurement of a first sample in accordance with various embodiments of the present disclosure.
Figure 6:
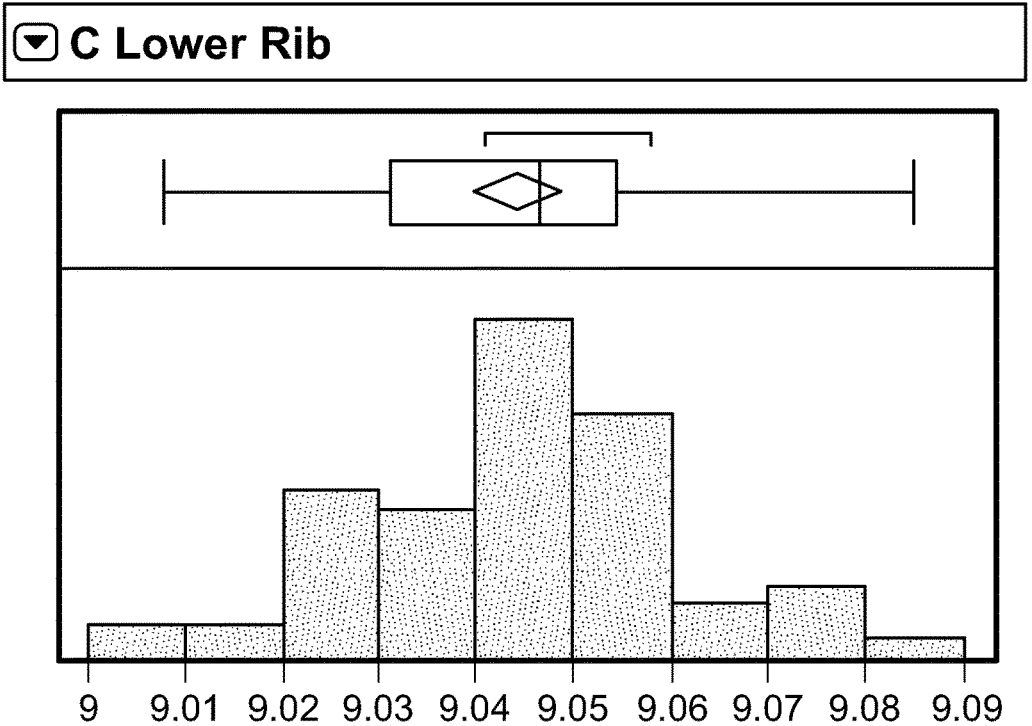
FIG. 6 is a histrograph of a lower rib diameter measurement of a first sample in accordance with various embodiments of the present disclosure.
Figure 7:
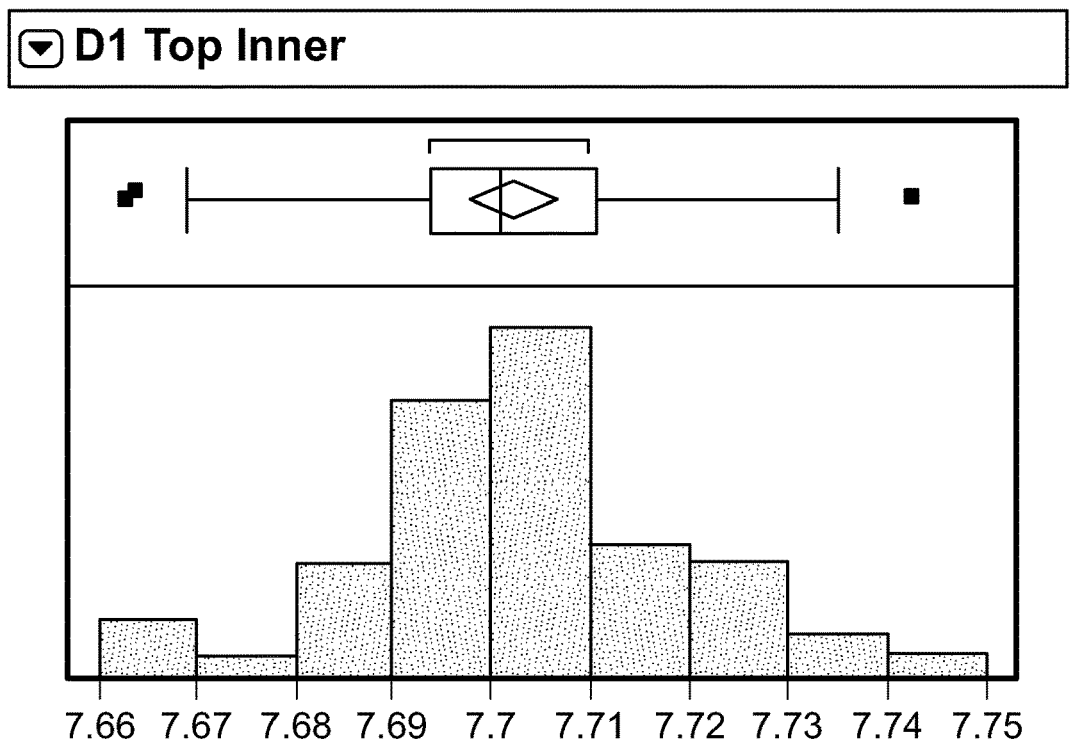
FIG. 7 is a histrograph of a top inner diameter measurement of a first sample in accordance with various embodiments of the present disclosure.
Figure 8:
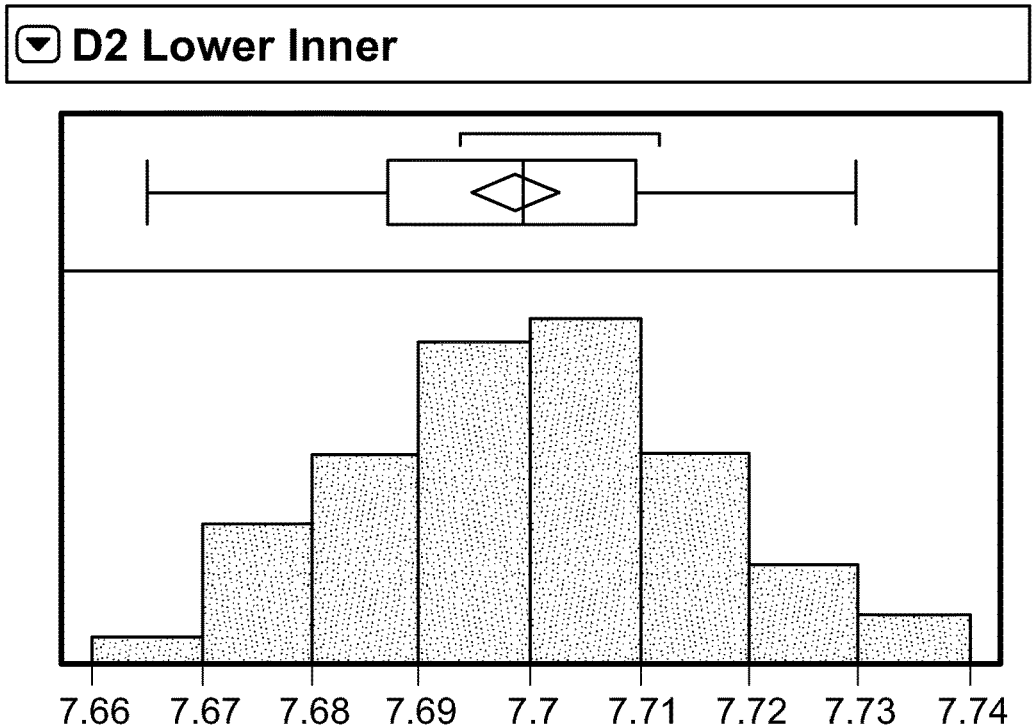
FIG. 8 is a histrograph of a lower inner diameter measurement of a first sample in accordance with various embodiments of the present disclosure.
Figure 9:
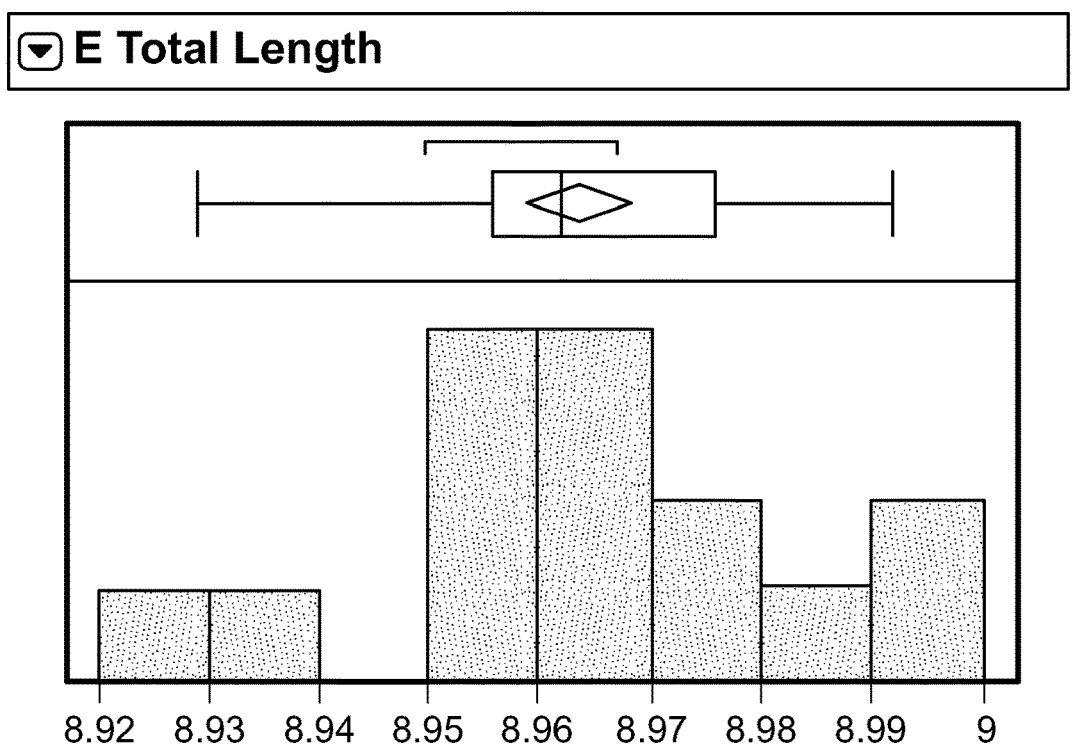
FIG. 9 is a histrograph of a total length measurement of a first sample in accordance with various embodiments of the present disclosure.
Figure 10:
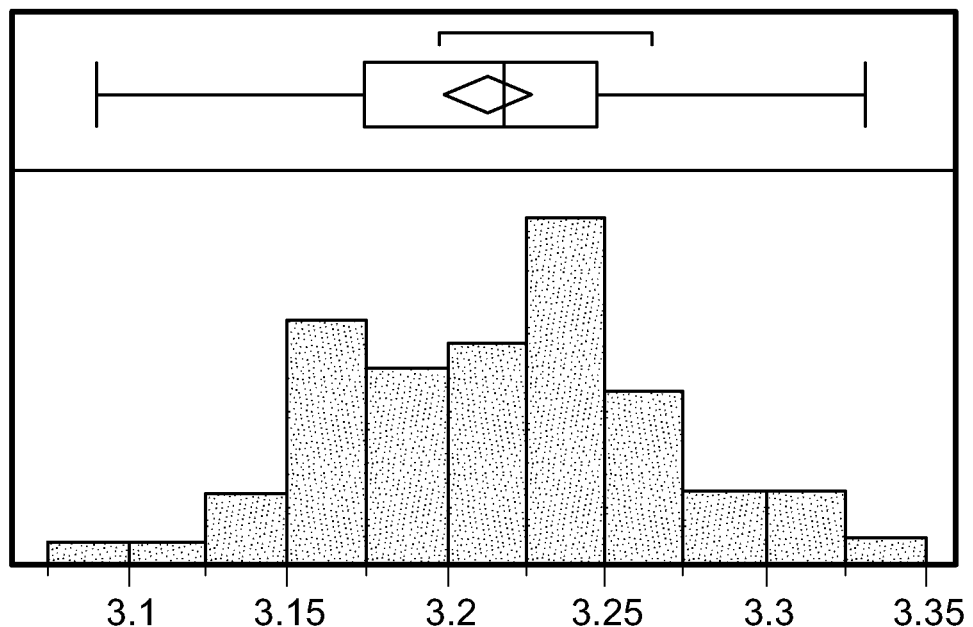
FIG. 10 is a histrograph of a top rib to middle rib measurement of a first sample in accordance with various embodiments of the present disclosure.
Figure 11:
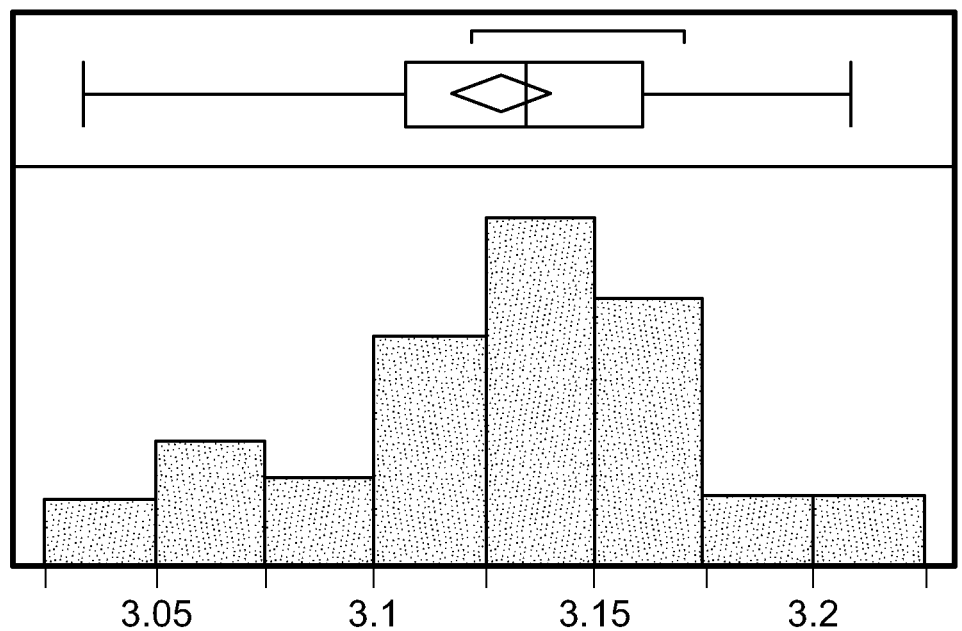
FIG. 11 is a histrograph of a middle rib to lower rib measurement of a first sample in accordance with various embodiments of the present disclosure.
Figure 12:
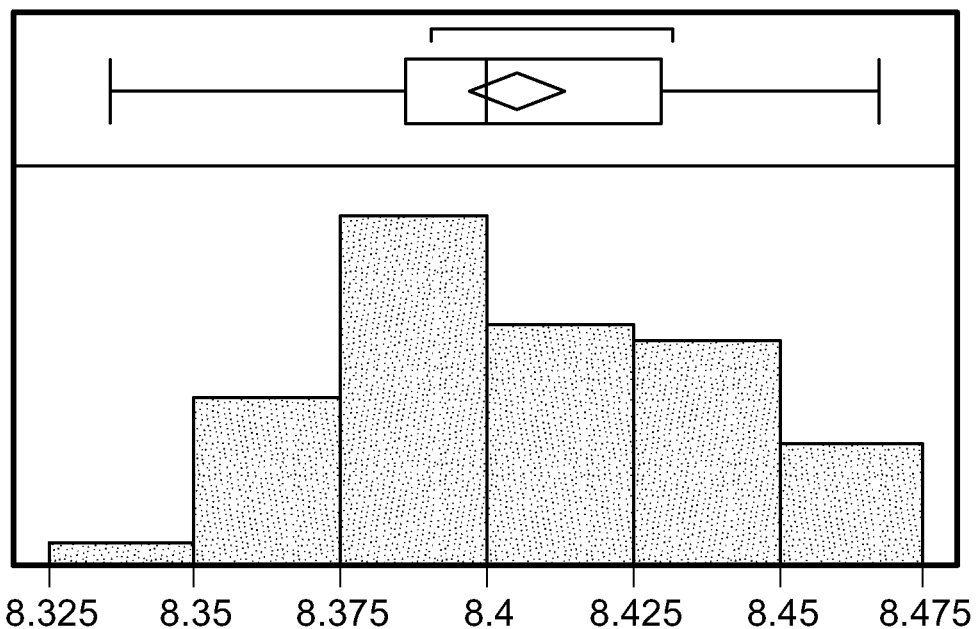
FIG. 12 is a histrograph of a bottom lip diameter measurement of a first sample in accordance with various embodiments of the present disclosure.
Figure 13:
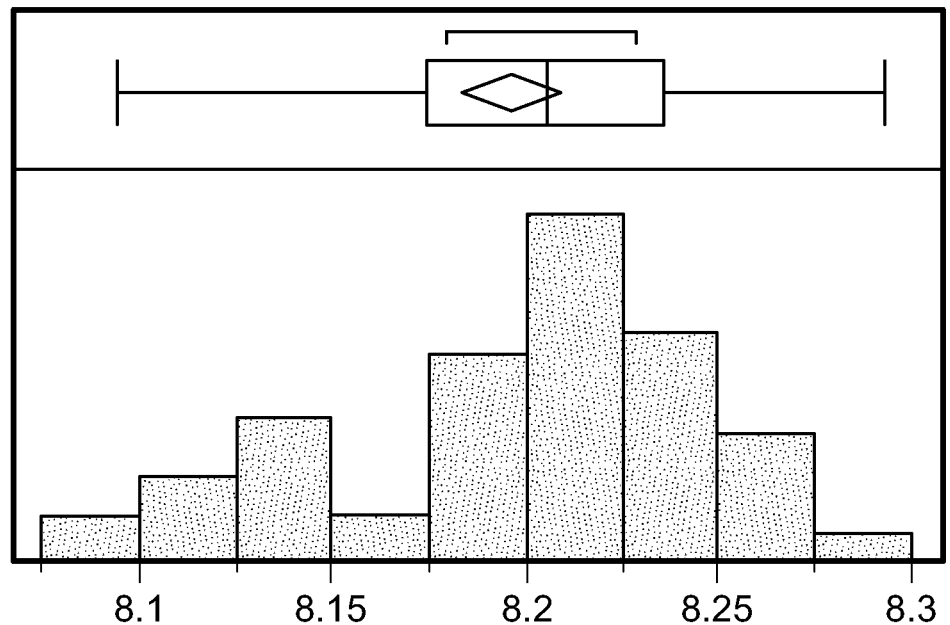
FIG. 13 is a histrograph of an inner lip diameter measurement of a second sample in accordance with various embodiments of the present disclosure.
Figure 14:
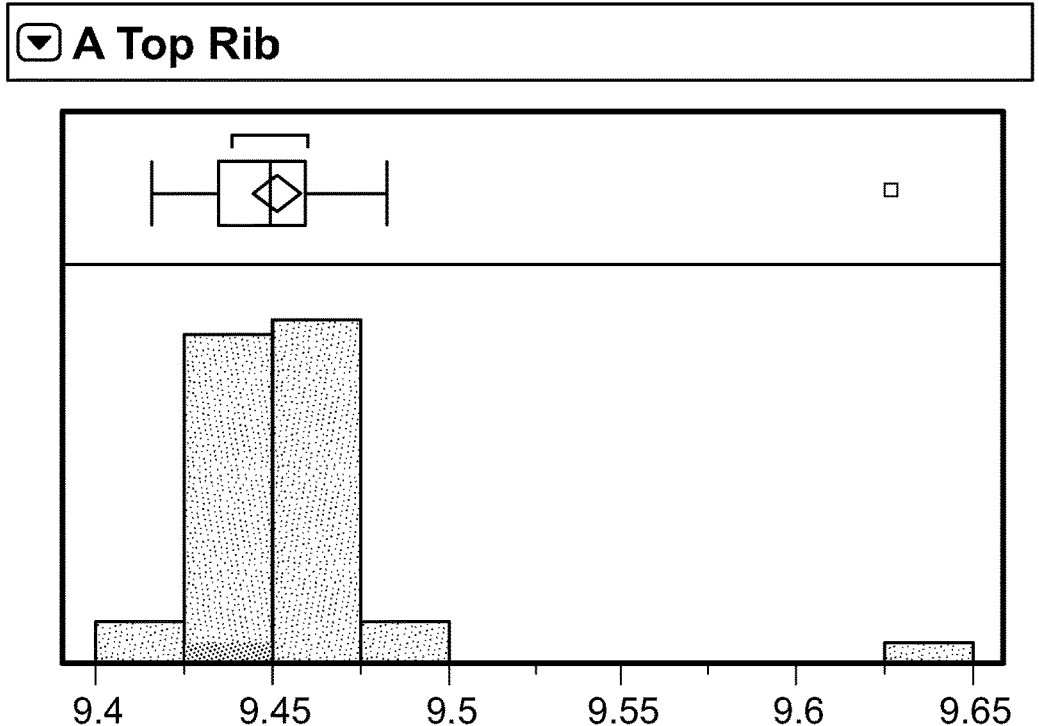
FIG. 14 is a histrograph of a top rib diameter measurement of a second sample in accordance with various embodiments of the present disclosure.
Figure 15:
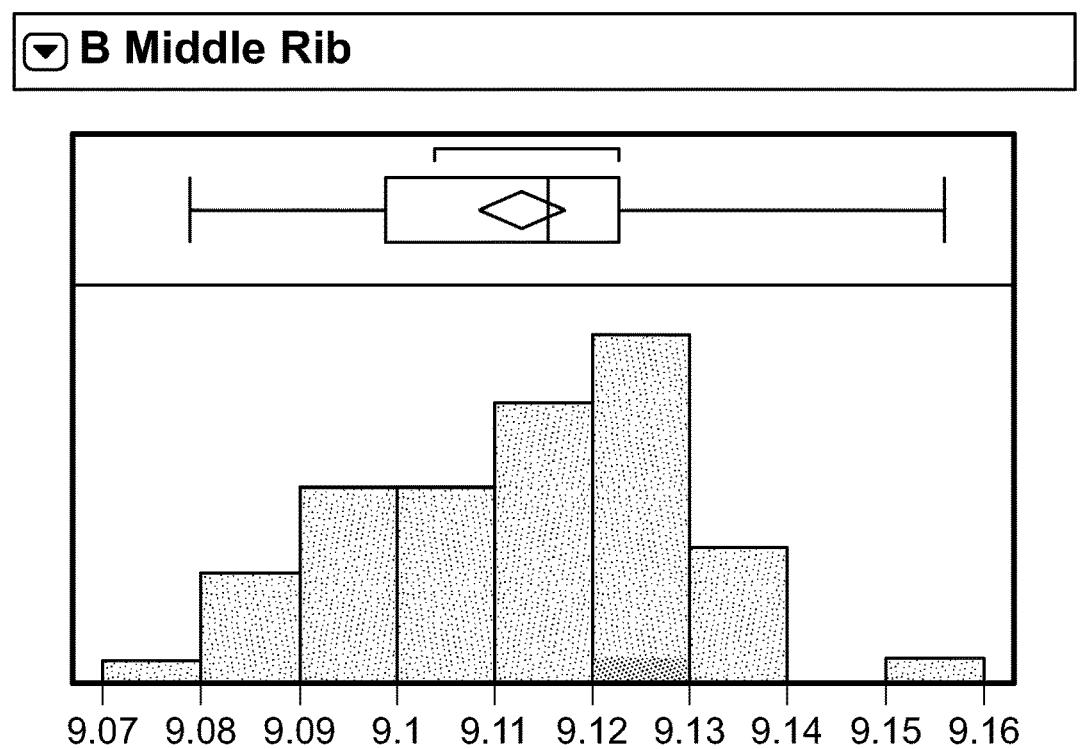
FIG. 15 is a histrograph of a middle rib diameter measurement of a second sample in accordance with various embodiments of the present disclosure.
Figure 16:
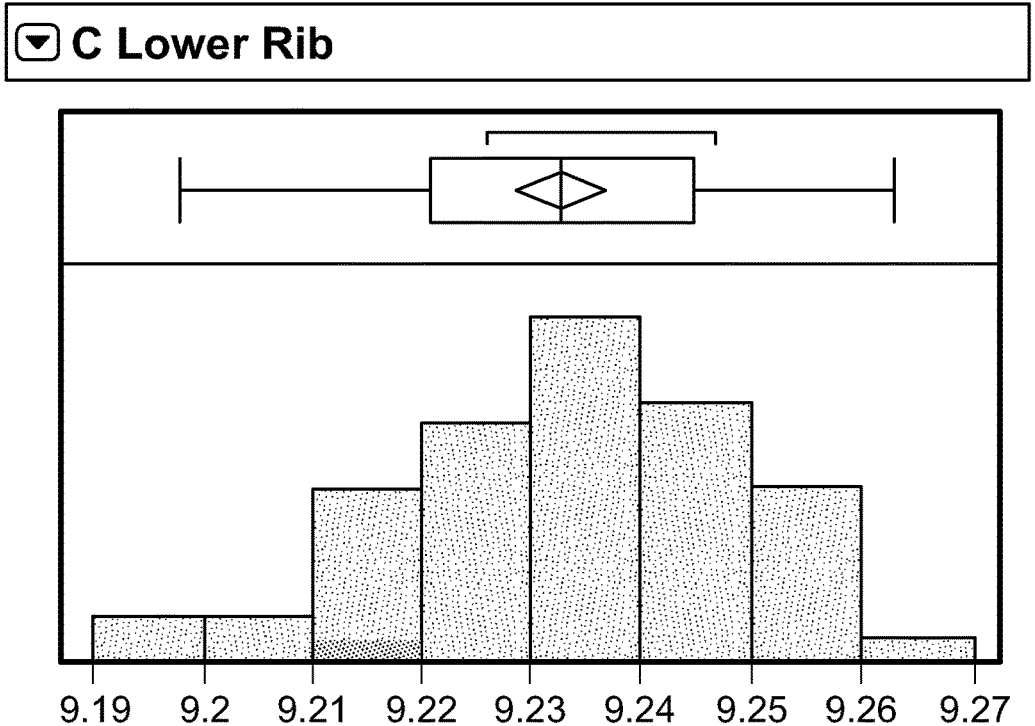
FIG. 16 is a histrograph of a lower rib diameter measurement of a second sample in accordance with various embodiments of the present disclosure.
Figure 17:
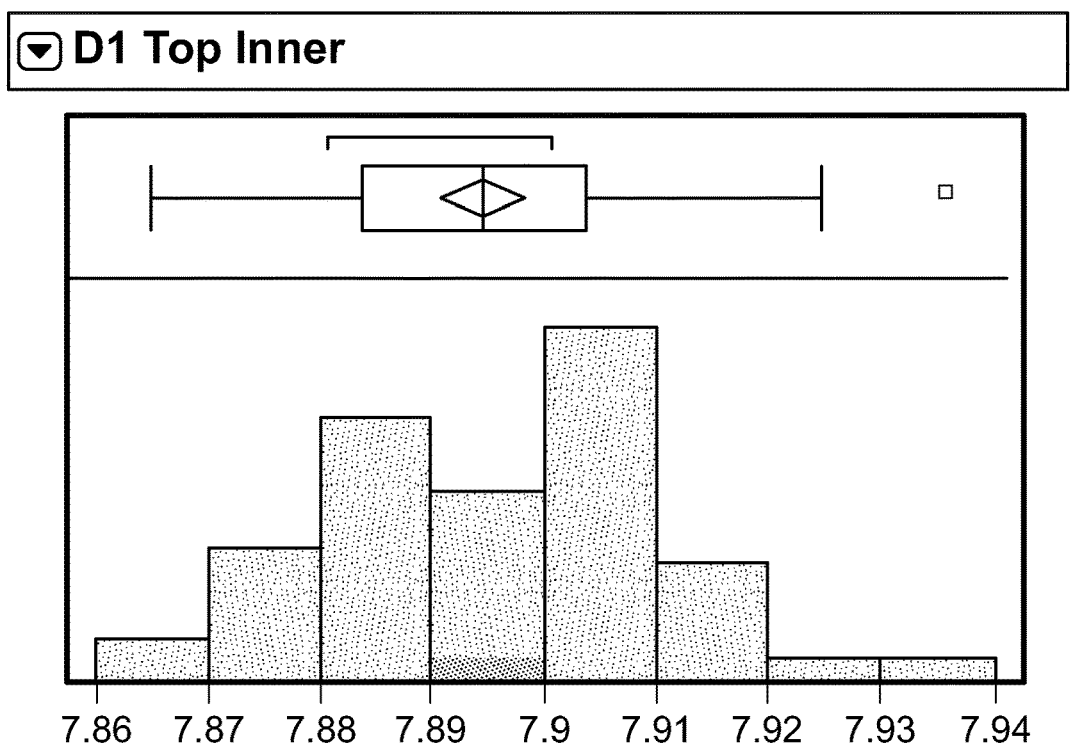
FIG. 17 is a histrograph of a top inner diameter measurement of a second sample in accordance with various embodiments of the present disclosure.
Figure 18:
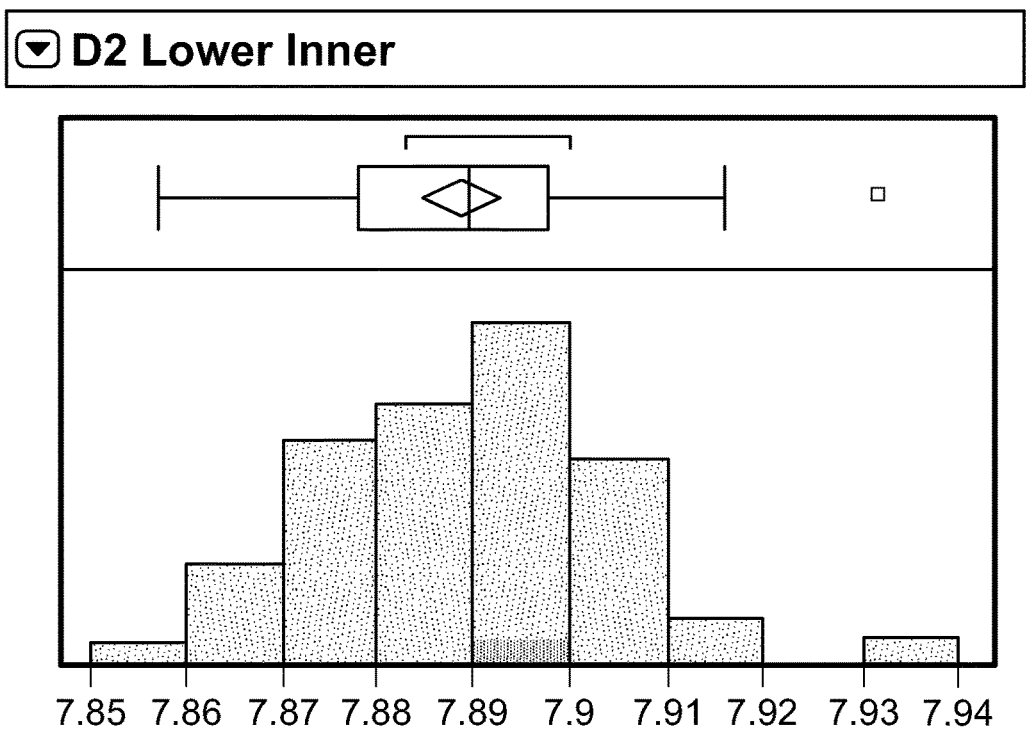
FIG. 18 is a histrograph of a lower inner diameter measurement of a second sample in accordance with various embodiments of the present disclosure.
Figure 19:
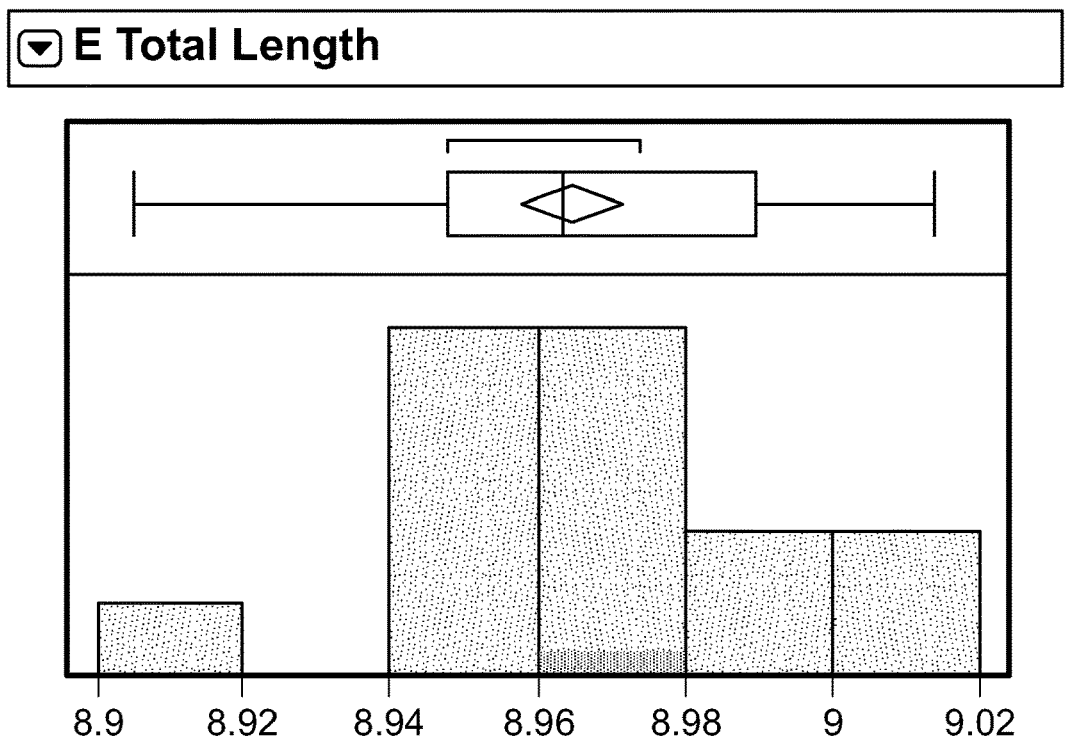
FIG. 19 is a histrograph of a total length measurement of a second sample in accordance with various embodiments of the present disclosure.
Figure 20:
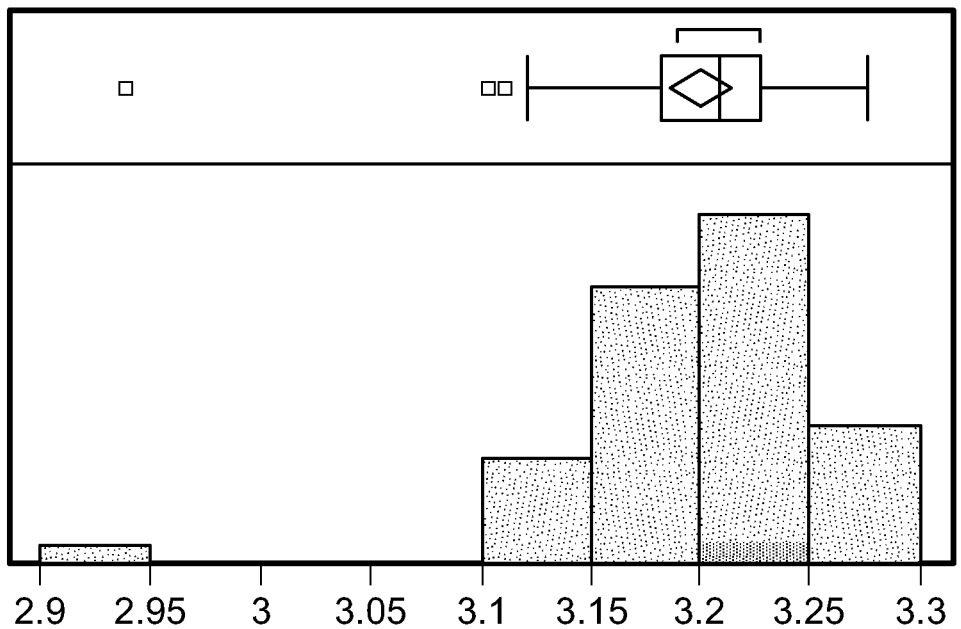
FIG. 20 is a histrograph of a top rib to middle rib measurement of a second sample in accordance with various embodiments of the present disclosure.
Figure 21:
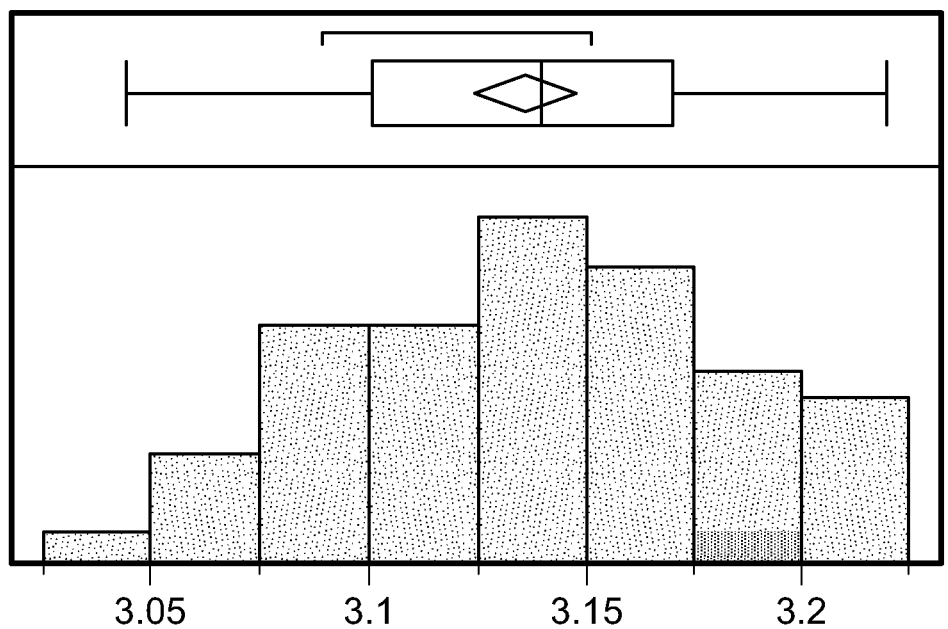
FIG. 21 is a histrograph of a middle rib to lower rib measurement of a second sample in accordance with various embodiments of the present disclosure.
Figure 22:
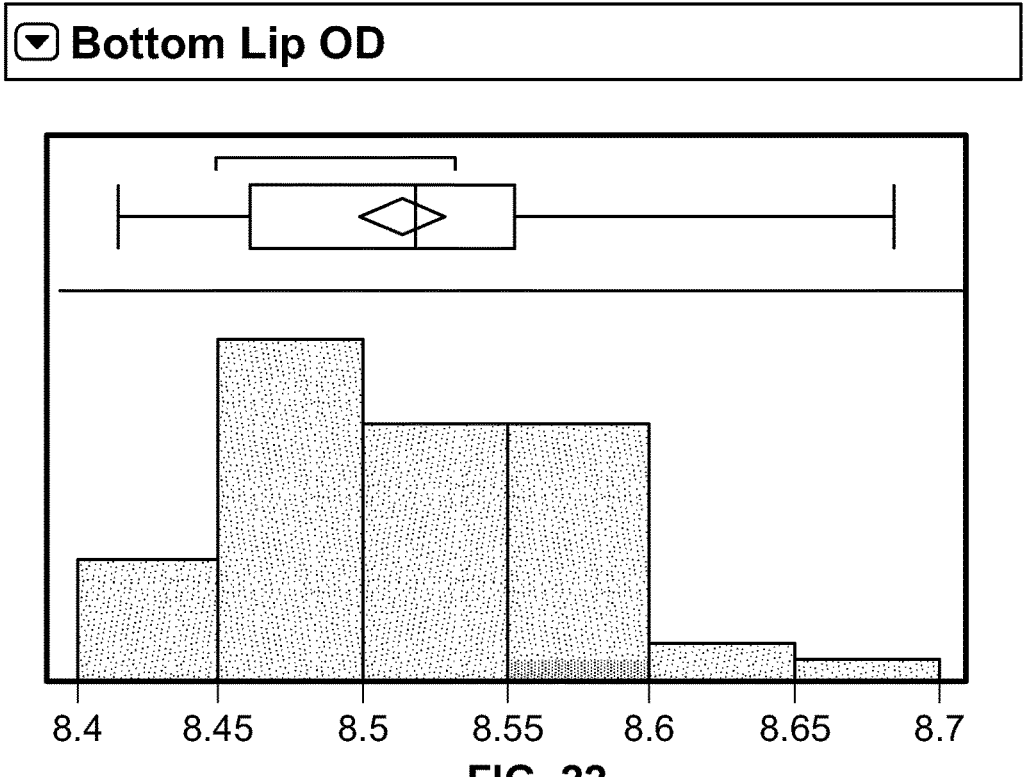
FIG. 22 is a histrograph of a bottom lip diameter measurement of a second sample in accordance with various embodiments of the present disclosure.
Figure 23:
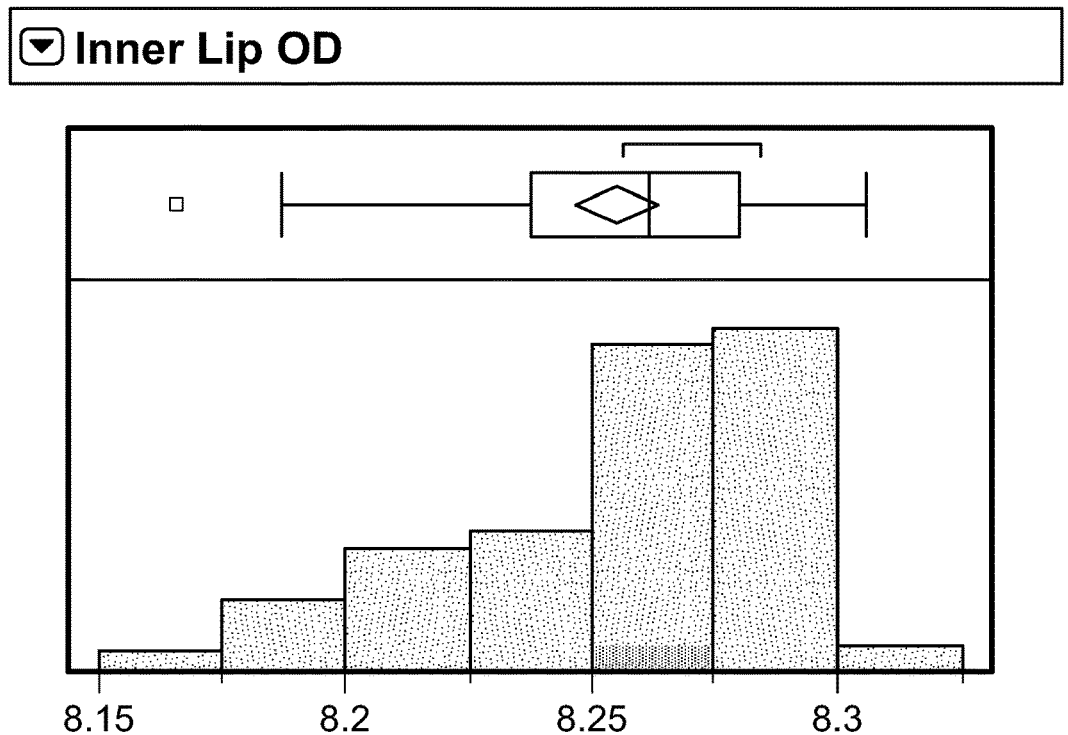
FIG. 23 is a histrograph of an inner lip diameter measurement of a second sample in accordance with various embodiments of the present disclosure.

Among particular illustrative proteins are the specific proteins set forth below, including fusions, fragments, analogs, variants or derivatives thereof:

OPGL specific antibodies, peptibodies, and related proteins, and the like (also referred to as RANKL specific antibodies, peptibodies and the like), including fully humanized and human OPGL specific antibodies, particularly fully humanized monoclonal antibodies, including but not limited to the antibodies described in PCT Publication No. WO 03/002713, which is incorporated herein in its entirety as to OPGL specific antibodies and antibody related proteins, particularly those having the sequences set forth therein, particularly, but not limited to, those denoted therein: 9H7; 18B2; 2D8; 2E11; 16E1; and 22B3, including the OPGL specific antibodies having either the light chain of sequence identification number:2 as set forth therein in FIG. 2 and/or the heavy chain of sequence identification number:4, as set forth therein in FIG. 4, each of which is individually and specifically incorporated by reference herein in its entirety fully as disclosed in the foregoing publication;

Myostatin binding proteins, peptibodies, and related proteins, and the like, including myostatin specific peptibodies, particularly those described in U.S. Publication No. 2004/0181033 and PCT Publication No. WO 2004/058988, which are incorporated by reference herein in their entirety particularly in parts pertinent to myostatin specific peptibodies, including but not limited to peptibodies of the mTN8-19 family, including those of sequence identification numbers: 305-351, including TN8-19-1 through TN8-19-40, TN8-19 con1 and TN8-19 con2; peptibodies of the mL2 family of sequence identification numbers:357-383; the mL15 family of sequence identification numbers:384-409; the mL17 family of sequence identification numbers:410-438; the mL20 family of sequence identification numbers:439-446; the mL21 family of sequence identification numbers:447-452; the mL24 family of sequence identification numbers:453-454; and those of sequence identification numbers:615-631, each of which is individually and specifically incorporated by reference herein in their entirety fully as disclosed in the foregoing publication;

IL-4 receptor specific antibodies, peptibodies, and related proteins, and the like, particularly those that inhibit activities mediated by binding of IL-4 and/or IL-13 to the receptor, including those described in PCT Publication No. WO 2005/047331 or PCT Application No. PCT/US2004/37242 and in U.S. Publication No. 2005/112694, which are incorporated herein by reference in their entirety particularly in parts pertinent to IL-4 receptor specific antibodies, particularly such antibodies as are described therein, particularly, and without limitation, those designated therein: L1H1; L1H2; L1H3; L1H4; L1H5; L1H6; L1H7; L1H8; L1H9; L1H10; L1H11; L2H1; L2H2; L2H3; L2H4; L2H5; L2H6; L2H7; L2H8; L2H9; L2H10; L2H11; L2H12; L2H13; L2H14; L3H1; L4H1; L5H1; L6H1, each of which is individually and specifically incorporated by reference herein in its entirety fully as disclosed in the foregoing publication;

Interleukin 1-receptor 1 ("IL1-R1") specific antibodies, peptibodies, and related proteins, and the like, including but not limited to those described in U.S. Publication No. 2004/097712, which is incorporated herein by reference in its entirety in parts pertinent to IL1-R1 specific binding proteins, monoclonal antibodies in particular, especially, without limitation, those designated therein: 15CA, 26F5, 27F2, 24E12, and 10H7, each of which is individually and specifically incorporated by reference herein in its entirety fully as disclosed in the aforementioned publication;

Ang2 specific antibodies, peptibodies, and related proteins, and the like, including but not limited to those described in PCT Publication No. WO 03/057134 and U.S. Publication No. 2003/0229023, each of which is incorporated herein by reference in its entirety particularly in parts pertinent to Ang2 specific antibodies and peptibodies and the like, especially those of sequences described therein and including but not limited to: L1(N); L1(N) WT; L1(N) 1K WT; 2×L1(N); 2×L1(N) WT; Con4 (N), Con4 (N) 1K WT, 2×Con4 (N) 1K; L1C; L1C 1K; 2×L1C; Con4C; Con4C 1K; 2×Con4C 1K; Con4-L1 (N); Con4-L1C; TN-12-9 (N); C17 (N); TN8-8(N); TN8-14 (N); Con 1 (N), also including anti-Ang 2 antibodies and formulations such as those described in PCT Publication No. WO 2003/030833 which is incorporated herein by reference in its entirety as to the same, particularly Ab526; Ab528; Ab531; Ab533; Ab535; Ab536; Ab537; Ab540; Ab543; Ab544; Ab545; Ab546; A551; Ab553; Ab555; Ab558; Ab559; Ab565; AbF1AbFD; AbFE; AbFJ; AbFK; AbG1D4; AbGC1E8; AbH1C12; AbIA1; AbF; AbIK, AbIP; and AbIP, in their various permutations as described therein, each of which is individually and specifically incorporated by reference herein in its entirety fully as disclosed in the foregoing publication;

NGF specific antibodies, peptibodies, and related proteins, and the like including, in particular, but not limited to those described in U.S. Publication No. 2005/0074821 and U.S. Pat. No. 6,919,426, which are incorporated herein by reference in their entirety particularly as to NGF-specific antibodies and related proteins in this regard, including in particular, but not limited to, the NGF-specific antibodies therein designated 4D4, 4G6, 6H9, 7H2, 14D10 and 14D11, each of which is individually and specifically incorporated by reference herein in its entirety fully as disclosed in the foregoing publication;

CD22 specific antibodies, peptibodies, and related proteins, and the like, such as those described in U.S. Pat. No. 5,789,554, which is incorporated herein by reference in its entirety as to CD22 specific antibodies and related proteins, particularly human CD22 specific antibodies, such as but not limited to humanized and fully human antibodies, including but not limited to humanized and fully human monoclonal antibodies, particularly including but not limited to human CD22 specific IgG antibodies, such as, for instance, a dimer of a human-mouse monoclonal hLL2 gamma-chain disulfide linked to a human-mouse monoclonal hLL2 kappa-chain, including, but limited to, for example, the human CD22 specific fully humanized antibody in Epratuzumab, CAS registry number 501423-23-0;

IGF-1 receptor specific antibodies, peptibodies, and related proteins, and the like, such as those described in PCT Publication No. WO 06/069202, which is incorporated herein by reference in its entirety as to IGF-1 receptor specific antibodies and related proteins, including but not limited to the IGF-1 specific antibodies therein designated L1H1, L2H2, L3H3, L4H4, L5H5, L6H6, L7H7, L8H8, L9H9, L10H10, L11H11, L12H12, L13H13, L14H14, L15H15, L16H16, L17H17, L18H18, L19H19, L20H20, L21H21, L22H22, L23H23, L24H24, L25H25, L26H26, L27H27, L28H28, L29H29, L30H30, L31H31, L32H32, L33H33, L34H34, L35H35, L36H36, L37H37, L38H38, L39H39, L40H40, L41H41, L42H42, L43H43, L44H44, L45H45, L46H46, L47H47, L48H48, L49H49, L50H50, L51H51, L52H52, and IGF-1R-binding fragments and derivatives thereof, each of which is individually and specifically incorporated by reference herein in its entirety fully as disclosed in the foregoing publication;

Also among non-limiting examples of anti-IGF-1R antibodies for use in the methods and compositions of the present invention are each and all of those described in:

(i) U.S. Publication No. 2006/0040358 (published Feb. 23, 2006), 2005/0008642 (published Jan. 13, 2005), 2004/0228859 (published Nov. 18, 2004), including but not limited to, for instance, antibody 1A (DSMZ Deposit No. DSM ACC 2586), antibody 8 (DSMZ Deposit No. DSM ACC 2589), antibody 23 (DSMZ Deposit No. DSM ACC 2588) and antibody 18 as described therein;

(ii) PCT Publication No. WO 06/138729 (published Dec. 28, 2006) and WO 05/016970 (published Feb. 24, 2005), and Lu et al. (2004), J. Biol. Chem. 279:2856-2865, including but not limited to antibodies 2F8, A12, and IMC-A12 as described therein;

(iii) PCT Publication No. WO 07/012614 (published Feb. 1, 2007), WO 07/000328 (published Jan. 4, 2007), WO 06/013472 (published Feb. 9, 2006), WO 05/058967 (published Jun. 30, 2005), and WO 03/059951 (published Jul. 24, 2003);

(iv) U.S. Publication No. 2005/0084906 (published Apr. 21, 2005), including but not limited to antibody 7C10, chimaeric antibody C7C10, antibody h7C10, antibody 7H2M, chimaeric antibody *7C10, antibody GM 607, humanized antibody 7C10 version 1, humanized antibody 7C10 version 2, humanized antibody 7C10 version 3, and antibody 7H2HM, as described therein;

(v) U.S. Publication Nos. 2005/0249728 (published Nov. 10, 2005), 2005/0186203 (published Aug. 25, 2005), 2004/0265307 (published Dec. 30, 2004), and 2003/0235582 (published Dec. 25, 2003) and Maloney et al. (2003), Cancer Res. 63:5073-5083, including but not limited to antibody EM164, resurfaced EM164, humanized EM164, huEM164 v1.0, huEM164 v1.1, huEM164 v1.2, and huEM164 v1.3 as described therein;

(vi) U.S. Pat. No. 7,037,498 (issued May 2, 2006), U.S. Publication Nos. 2005/0244408 (published Nov. 30, 2005) and 2004/0086503 (published May 6, 2004), and Cohen, et al. (2005), Clinical Cancer Res. 11:2063-2073, e.g., antibody CP-751,871, including but not limited to each of the antibodies produced by the hybridomas having the ATCC accession numbers PTA-2792, PTA-2788, PTA-2790, PTA-2791, PTA-2789, PTA-2793, and antibodies 2.12.1, 2.13.2, 2.14.3, 3.1.1, 4.9.2, and 4.17.3, as described therein;

(vii) U.S. Publication Nos. 2005/0136063 (published Jun. 23, 2005) and 2004/0018191 (published Jan. 29, 2004), including but not limited to antibody 19D12 and an antibody comprising a heavy chain encoded by a polynucleotide in plasmid 15H12/19D12 HCA (γ4), deposited at the ATCC under number PTA-5214, and a light chain encoded by a polynucleotide in plasmid 15H12/19D12 LCF (κ), deposited at the ATCC under number PTA-5220, as described therein; and (viii) U.S. Publication No. 2004/0202655 (published Oct. 14, 2004), including but not limited to antibodies PINT-6A1, PINT-7A2, PINT-7A4, PINT-7A5, PINT-7A6, PINT-8A1, PINT-9A2, PINT-11A1, PINT-11A2, PINT-11A3, PINT-11A4, PINT-11A5, PINT-11A7, PINT-11A12, PINT-12A1, PINT-12A2, PINT-12A3, PINT-12A4, and PINT-12A5, as described therein; each and all of which are herein incorporated by reference in their entireties, particularly as to the aforementioned antibodies, peptibodies, and related proteins and the like that target IGF-1 receptors;

B-7 related protein 1 specific antibodies, peptibodies, related proteins and the like ("B7RP-1," also is referred to in the literature as B7H2, ICOSL, B7h, and CD275), particularly B7RP-specific fully human monoclonal IgG2 antibodies, particularly fully human IgG2 monoclonal antibody that binds an epitope in the first immunoglobulin-like domain of B7RP-1, especially those that inhibit the interaction of B7RP-1 with its natural receptor, ICOS, on activated T cells in particular, especially, in all of the foregoing regards, those disclosed in U.S. Publication No. 2008/0166352 and PCT Publication No. WO 07/011941, which are incorporated herein by reference in their entireties as to such antibodies and related proteins, including but not limited to antibodies designated therein as follow: 16H (having light chain variable and heavy chain variable sequences sequence identification number:1 and sequence identification number:7 respectively therein); 5D (having light chain variable and heavy chain variable sequences sequence identification number:2 and sequence identification number:9 respectively therein); 2H (having light chain variable and heavy chain variable sequences sequence identification number:3 and sequence identification number:10 respectively therein); 43H (having light chain variable and heavy chain variable sequences sequence identification number:6 and sequence identification number:14 respectively therein); 41H (having light chain variable and heavy chain variable sequences sequence identification number:5 and sequence identification number:13 respectively therein); and 15H (having light chain variable and heavy chain variable sequences sequence identification number:4 and sequence identification number:12 respectively therein), each of which is individually and specifically incorporated by reference herein in its entirety fully as disclosed in the foregoing publication;

IL-15 specific antibodies, peptibodies, and related proteins, and the like, such as, in particular, humanized monoclonal antibodies, particularly antibodies such as those disclosed in U.S. Publication Nos. 2003/0138421; 2003/023586; and 2004/0071702; and U.S. Pat. No. 7,153,507, each of which is incorporated herein by reference in its entirety as to IL-15 specific antibodies and related proteins, including peptibodies, including particularly, for instance, but not limited to, HuMax IL-15 antibodies and related proteins, such as, for instance, 14687;

IFN gamma specific antibodies, peptibodies, and related proteins and the like, especially human IFN gamma specific antibodies, particularly fully human anti-IFN gamma antibodies, such as, for instance, those described in U.S. Publication No. 2005/0004353, which is incorporated herein by reference in its entirety as to IFN gamma specific antibodies, particularly, for example, the antibodies therein designated 1118; 1118*; 1119; 1121; and 1121*. The entire sequences of the heavy and light chains of each of these antibodies, as well as the sequences of their heavy and light chain variable regions and complementarity determining regions, are each individually and specifically incorporated by reference herein in its entirety fully as disclosed in the foregoing publication and in Thakur et al. (1999), Mol. Immunol. 36:1107-1115. In addition, description of the properties of these antibodies provided in the foregoing publication is also incorporated herein by reference in its entirety. Specific antibodies include those having the heavy chain of sequence identification number:17 and the light chain of sequence identification number:18; those having the heavy chain variable region of sequence identification number:6 and the light chain variable region of sequence identification number:8; those having the heavy chain of sequence identification number:19 and the light chain of sequence identification number:20; those having the heavy chain variable region of sequence identification number:10 and the light chain variable region of sequence identification number:12; those having the heavy chain of sequence identification number:32 and the light chain of sequence identification number:20; those having the heavy chain variable region of sequence identification number:30 and the light chain variable region of sequence identification number:12; those having the heavy chain sequence of sequence identification number:21 and the light chain sequence of sequence identification number:22; those having the heavy chain variable region of sequence identification number:14 and the light chain variable region of sequence identification number:16; those having the heavy chain of sequence identification number:21 and the light chain of sequence identification number:33; and those having the heavy chain variable region of sequence identification number:14 and the light chain variable region of sequence identification number:31, as disclosed in the foregoing publication. A specific antibody contemplated is antibody 1119 as disclosed in the foregoing U.S. publication and having a complete heavy chain of sequence identification number:17 as disclosed therein and having a complete light chain of sequence identification number:18 as disclosed therein;

TALL-1 specific antibodies, peptibodies, and the related proteins, and the like, and other TALL specific binding proteins, such as those described in U.S. Publication Nos. 2003/0195156 and 2006/0135431, each of which is incorporated herein by reference in its entirety as to TALL-1 binding proteins, particularly the molecules of Tables 4 and 5B, each of which is individually and specifically incorporated by reference herein in its entirety fully as disclosed in the foregoing publications;

Parathyroid hormone ("PTH") specific antibodies, peptibodies, and related proteins, and the like, such as those described in U.S. Pat. No. 6,756,480, which is incorporated herein by reference in its entirety, particularly in parts pertinent to proteins that bind PTH;

Thrombopoietin receptor ("TPO-R") specific antibodies, peptibodies, and related proteins, and the like, such as those described in U.S. Pat. No. 6,835,809, which is herein incorporated by reference in its entirety, particularly in parts pertinent to proteins that bind TPO-R;

Hepatocyte growth factor ("HGF") specific antibodies, peptibodies, and related proteins, and the like, including those that target the HGF/SF:cMet axis (HGF/SF:c-Met), such as the fully human monoclonal antibodies that neutralize hepatocyte growth factor/scatter (HGF/SF) described in U.S. Publication No. 2005/0118643 and PCT Publication No. WO 2005/017107, huL2G7 described in U.S. Pat. No. 7,220,410 and OA-5d5 described in U.S. Pat. Nos. 5,686,292 and 6,468,529 and in PCT Publication No. WO 96/38557, each of which is incorporated herein by reference in its entirety, particularly in parts pertinent to proteins that bind HGF;

TRAIL-R2 specific antibodies, peptibodies, related proteins and the like, such as those described in U.S. Pat. No. 7,521,048, which is herein incorporated by reference in its entirety, particularly in parts pertinent to proteins that bind TRAIL-R2;

Activin A specific antibodies, peptibodies, related proteins, and the like, including but not limited to those described in U.S. Publication No. 2009/0234106, which is herein incorporated by reference in its entirety, particularly in parts pertinent to proteins that bind Activin A;

TGF-beta specific antibodies, peptibodies, related proteins, and the like, including but not limited to those described in U.S. Pat. No. 6,803,453 and U.S. Publication No. 2007/0110747, each of which is herein incorporated by reference in its entirety, particularly in parts pertinent to proteins that bind TGF-beta;

Amyloid-beta protein specific antibodies, peptibodies, related proteins, and the like, including but not limited to those described in PCT Publication No. WO 2006/081171, which is herein incorporated by reference in its entirety, particularly in parts pertinent to proteins that bind amyloid-beta proteins. One antibody contemplated is an antibody having a heavy chain variable region comprising sequence identification number:8 and a light chain variable region having sequence identification number:6 as disclosed in the foregoing publication;

c-Kit specific antibodies, peptibodies, related proteins, and the like, including but not limited to those described in U.S. Publication No. 2007/0253951, which is incorporated herein by reference in its entirety, particularly in parts pertinent to proteins that bind c-Kit and/or other stem cell factor receptors;

OX40L specific antibodies, peptibodies, related proteins, and the like, including but not limited to those described in U.S. Publication No. 2006/0002929, which is incorporated herein by reference in its entirety, particularly in parts pertinent to proteins that bind OX40L and/or other ligands of the OX40 receptor; and Other exemplary proteins, including Activase® (alteplase, tPA); Aranesp® (darbepoetin alfa); Epogen® (epoetin alfa, or erythropoietin); GLP-1, Avonex® (interferon beta-1a); Bexxar® (tositumomab, anti-CD22 monoclonal antibody); Betaseron® (interferon-beta); Campath® (alemtuzumab, anti-CD52 monoclonal antibody); Dynepo® (epoetin delta); Velcade® (bortezomib); MLN0002 (anti-α4β7 mAb); MLN1202 (anti-CCR2 chemokine receptor mAb); Enbrel® (etanercept, TNF-receptor/Fc fusion protein, TNF blocker); Eprex® (epoetin alfa); Erbitux® (cetuximab, anti-EGFR/HER1/c-ErbB-1); Genotropin® (somatropin, Human Growth Hormone); Herceptin® (trastuzumab, anti-HER2/neu (erbB2) receptor mAb); Humatrope® (somatropin, Human Growth Hormone); Humira® (adalimumab); insulin in solution; Infergen® (interferon alfacon-1); Natrecor® (nesiritide; recombinant human B-type natriuretic peptide (hBNP); Kineret® (anakinra); Leukine® (sargamostim, rhuGM-CSF); LymphoCide® (epratuzumab, anti-CD22 mAb); Benlysta™ (lymphostat B, belimumab, anti-BlyS mAb); Metalyse® (tenecteplase, t-PA analog); Mircera® (methoxy polyethylene glycol-epoetin beta); Mylotarg® (gemtuzumab ozogamicin); Raptiva® (efalizumab); Cimzia® (certolizumab pegol, CDP 870); Soliris™ (eculizumab); pexelizumab (anti-C5 complement); Numax® (MEDI-524); Lucentis® (ranibizumab); Panorex® (17-1A, edrecolomab); Trabio® (lerdelimumab); TheraCim hR3 (nimotuzumab); Omnitarg (pertuzumab, 2C4); Osidem® (IDM-1); OvaRex® (B43.13); Nuvion® (visilizumab); cantuzumab mertansine (huC242-DM1); NeoRecormon® (epoetin beta); Neumega® (oprelvekin, human interleukin-11); Neulasta® (pegylated filgastrim, pegylated G-CSF, pegylated hu-Met-G-CSF); Neupogen® (filgrastim, G-CSF, hu-MetG-CSF); Orthoclone OKT3® (muromonab-CD3, anti-CD3 monoclonal antibody); Procrit® (epoetin alfa); Remicade® (infliximab, anti-TNFα monoclonal antibody); Reopro® (abciximab, anti-GP IIb/IIIa receptor monoclonal antibody); Actemra® (anti-IL6 Receptor mAb); Avastin® (bevacizumab), HuMax-CD4 (zanolimumab); Rituxan® (rituximab, anti-CD20 mAb); Tarceva® (erlotinib); Roferon-A®-(interferon alfa-2a); Simulect® (basiliximab); Prexige® (lumiracoxib); Synagis® (palivizumab); 146B7-CHO (anti-IL15 antibody, see U.S. Pat. No. 7,153,507); Tysabri® (natalizumab, anti-α4integrin mAb); Valortim® (MDX-1303, anti-*B. anthracis* protective antigen mAb); ABthrax™; Vectibix® (panitumumab); Xolair® (omalizumab); ETI211 (anti-MRSA mAb); IL-1 trap (the Fc portion of human IgG1 and the extracellular domains of both IL-1 receptor components (the Type I receptor and receptor accessory protein)); VEGF trap (Ig domains of VEGFR1 fused to IgG1 Fc); Zenapax® (daclizumab); Zenapax® (daclizumab, anti-IL-2Ra mAb); Zevalin® (ibritumomab tiuxetan); Zetia® (ezetimibe); Orencia® (atacicept, TACI-Ig); anti-CD80 monoclonal antibody (galiximab); anti-CD23 mAb (lumiliximab); BR2-Fc (huBR3/huFc fusion protein, soluble BAFF antagonist); CNTO 148 (golimumab, anti-TNFα mAb); HGS-ETR1 (mapatumumab; human anti-TRAIL Receptor-1 mAb); HuMax-CD20 (ocrelizumab, anti-CD20 human mAb); HuMax-EGFR (zalutumumab); M200 (volociximab, anti-α5β1 integrin mAb); MDX-010 (ipilimumab, anti-CTLA-4 mAb and VEGFR-1 (IMC-18F1); anti-BR3 mAb; anti-*C. difficile* Toxin A and Toxin B C mAbs MDX-066 (CDA-1) and MDX-1388); anti-CD22 dsFv-PE38 conjugates (CAT-3888 and CAT-8015); anti-CD25 mAb (HuMax-TAC); anti-CD3 mAb (NI-0401); adecatumumab; anti-CD30 mAb (MDX-060); MDX-1333 (anti-IFNAR); anti-CD38 mAb (HuMax CD38); anti-CD40L mAb; anti-Cripto mAb; anti-CTGF Idiopathic Pulmonary Fibrosis Phase I Fibrogen (FG-3019); anti-CTLA4 mAb; anti-eotaxinl mAb (CAT-213); anti-FGF8 mAb; anti-ganglioside GD2 mAb; anti-ganglioside GM2 mAb; anti-GDF-8 human mAb (MYO-029); anti-GM-CSF Receptor mAb (CAM-3001); anti-HepC mAb (HuMax HepC); anti-IFNα mAb (MEDI-545, MDX-1103); anti-IGF1R mAb; anti-IGF-1R mAb (HuMax-Inflam); anti-IL12 mAb (ABT-874); anti-IL12/IL23 mAb (CNTO 1275); anti-IL13 mAb (CAT-354); anti-IL2Ra mAb (HuMax-TAC); anti-IL5 Receptor mAb; anti-integrin receptors mAb (MDX-018, CNTO 95); anti-IP10 Ulcerative Colitis mAb (MDX-1100); anti-LLY antibody; BMS-66513; anti-Mannose Receptor/hCGβ mAb (MDX-1307); anti-mesothelin dsFv-PE38 conjugate (CAT-5001); anti-PD1mAb (MDX-1106 (ONO-4538)); anti-PDGFRα antibody (IMC-3G3); anti-TGFß mAb (GC-1008); anti-TRAIL Receptor-2 human mAb (HGS-ETR2); anti-TWEAK mAb; anti-VEGFR/Flt-1 mAb; anti-ZP3 mAb (HuMax-ZP3); NVS Antibody #1; and NVS Antibody #2.

Also included can be a sclerostin antibody, such as but not limited to romosozumab, blosozumab, or BPS 804 (Novartis). Further included can be therapeutics such as rilotumumab, bixalomer, trebananib, ganitumab, conatumumab, motesanib diphosphate, brodalumab, vidupiprant, panitumumab, denosumab, NPLATE, PROLIA, VECTIBIX or XGEVA. Additionally, included in the device can be a monoclonal antibody (IgG) that binds human Proprotein Convertase Subtilisin/Kexin Type 9 (PCSK9). Such PCSK9 specific antibodies include, but are not limited to, Repatha® (evolocumab) and Praluent® (alirocumab), as well as molecules, variants, analogs or derivatives thereof as disclosed in the following patents or patent applications, each of which is herein incorporated by reference in its entirety for all purposes: U.S. Pat. No. 8,030,547, U.S. Publication No. 2013/0064825, WO2008/057457, WO2008/057458, WO2008/057459, WO2008/063382, WO2008/133647, WO2009/100297, WO2009/100318, WO2011/037791, WO2011/053759, WO2011/053783, WO2008/125623, WO2011/072263, WO2009/055783, WO2012/0544438, WO2010/029513, WO2011/111007, WO2010/077854, WO2012/088313, WO2012/101251, WO2012/101252, WO2012/101253, WO2012/109530, and WO2001/031007.

Also included can be talimogene laherparepvec or another oncolytic HSV for the treatment of melanoma or other cancers. Examples of oncolytic HSV include, but are not limited to talimogene laherparepvec (U.S. Pat. Nos. 7,223,593 and 7,537,924); OncoVEXGALV/CD (U.S. Pat. No. 7,981,669); OrienX010 (Lei et al. (2013), World J. Gastroenterol., 19:5138-5143); G207, 1716; NV1020; NV12023; NV1034 and NV1042 (Vargehes et al. (2002), Cancer Gene Ther., 9(12):967-978).

Also included are TIMPs. TIMPs are endogenous tissue inhibitors of metalloproteinases (TIMPs) and are important in many natural processes. TIMP-3 is expressed by various cells or and is present in the extracellular matrix; it inhibits all the major cartilage-degrading metalloproteases, and may play a role in role in many degradative diseases of connective tissue, including rheumatoid arthritis and osteoarthritis, as well as in cancer and cardiovascular conditions. The amino acid sequence of TIMP-3, and the nucleic acid sequence of a DNA that encodes TIMP-3, are disclosed in U.S. Pat. No. 6,562,596, issued May 13, 2003, the disclosure of which is incorporated by reference herein. Description of TIMP mutations can be found in U.S. Publication No. 2014/0274874 and PCT Publication No. WO 2014/152012.

Also included are antagonistic antibodies for human calcitonin gene-related peptide (CGRP) receptor and bispecific antibody molecule that target the CGRP receptor and other headache targets. Further information concerning these molecules can be found in PCT Application No. WO 2010/075238.

Additionally, bispecific T cell engager (BiTE®) antibodies, e.g. BLINCYTO® (blinatumomab), can be used in the device. Alternatively, included can be an APJ large molecule agonist e.g., apelin or analogues thereof in the device. Information relating to such molecules can be found in PCT Publication No. WO 2014/099984.

In certain embodiments, the medicament comprises a therapeutically effective amount of an anti-thymic stromal lymphopoietin (TSLP) or TSLP receptor antibody. Examples of anti-TSLP antibodies that may be used in such embodiments include, but are not limited to, those described in U.S. Pat. Nos. 7,982,016, and 8,232,372, and U.S. Publication No. 2009/0186022. Examples of anti-TSLP receptor antibodies include, but are not limited to, those described in U.S. Pat. No. 8,101,182. In particularly preferred embodiments, the medicament comprises a therapeutically effective amount of the anti-TSLP antibody designated as A5 within U.S. Pat. No. 7,982,016.

Although the plungers, drug delivery assemblies, drug delivery mechanisms, methods, and elements thereof, have been described in terms of exemplary embodiments, they are not limited thereto. The detailed description is to be construed as exemplary only and does not describe every possible embodiment of the invention because describing every possible embodiment would be impractical, if not impossible. Those skilled in the art will recognize that a wide variety of modifications, alterations, and combinations can be made with respect to the above described embodiments without departing from the scope of the invention, and that such modifications, alterations, and combinations are to be viewed as being within the ambit of the inventive concept. Numerous alternative embodiments could be implemented, using either current technology or technology developed after the filing date of this patent that would still fall within the scope of the claims defining the invention.

It should be understood that the legal scope of the invention is defined by the words of the claims set forth at the end of this patent. The appended claims should be construed broadly to include other variants and embodiments of same, which may be made by those skilled in the art without departing from the scope and range of embodiments described herein.

What is claimed is:

1. A plunger for use in a drug delivery device, the plunger comprising:
    a body portion having a sidewall, a leading surface, and a trailing surface, wherein the body portion does not include a cavity having an opening defined in the trailing surface configured to receive a plunger rod therein;
    a ribbed portion comprising a plurality of ribs projecting radially outwardly from the sidewall of the body portion and spaced axially apart from one another, the plurality of ribs comprising at least a trailing rib and a leading rib, each of the ribs including an annular configuration;
    wherein the body portion is configured to occupy a first configuration in the absence of an axial load, and a second configuration in the presence of an axial load, compression from the axial load causing the body portion in the second configuration to have an axial dimension that is less than an axial dimension of the first configuration, and wherein the ribbed portion has a first radial dimension when the body portion occupies the first configuration and a second radial dimension when the body portion occupies the second configuration, the first and second radial dimensions being substantially equal.

2. The plunger of claim 1, wherein radial surfaces of the sidewall extending between the ribs have curved configurations.

3. The plunger of claim 2, wherein the radial surfaces of the sidewall extending between the ribs are concavely curved along a longitudinal axis of the body portion.

4. The plunger of claim 1, wherein radial surfaces of the body portion extending between the ribs include flat portions.

5. The plunger of claim 4, wherein the radial surfaces of the body portion extending between the ribs further include frustoconical portions on axial ends of the flat portions.

6. The plunger of claim 1, wherein a trim edge of the body portion is adjacent to the trailing surface thereof.

7. The plunger of claim 6, wherein the trim edge has an outer diameter less than outer diameters of the ribs.

8. The plunger of claim 1, wherein the leading surface includes a roughened portion.

9. The plunger of claim 1, wherein the leading surface as a generally cone-shaped configuration.

10. The plunger of claim 1, wherein at least one of the ribs has a curved axial profile.

11. The plunger of claim 1, wherein at least one of the ribs includes a cylindrical portion extending between curved, axial end portions thereof.

12. The plunger of claim 1, further comprising a plurality of protrusions extending away from the trailing surface of the body portion.

13. The plunger of claim 1, further comprising an intermediate rib disposed between the trailing rib and the leading rib, the intermediate rib having an annular configuration.

14. The plunger of claim 13, wherein the at least one of the trailing rib or the intermediate rib is axially smaller than the leading rib.

15. The plunger of claim 14, wherein both the trailing rib and the intermediate rib are axially smaller than the leading rib.

16. A drug delivery assembly comprising:
a plunger including:
- a body portion having a sidewall, a leading surface, and a trailing surface, wherein the body portion does not include a cavity having an opening defined in the trailing surface configured to receive a plunger rod therein, and
- a ribbed portion comprising a plurality of ribs projecting radially outwardly from the sidewall of the body portion and spaced axially apart from one another, the plurality of ribs comprising at least a trailing rib and a leading rib, each of the ribs including an annular configuration, wherein the body portion is configured to occupy a first configuration in the absence of an axial load, and a second configuration in the presence of an axial load, compression from the axial load causing the body portion in the second configuration to have an axial dimension that is less than an axial dimension of the first configuration, and wherein the ribbed portion has a first radial dimension when the body portion occupies the first configuration and a second radial dimension when the body portion occupies the second configuration, the first and second radial dimensions being substantially equal;

a chamber with an annular sidewall extending between a first, open end and a second end having a dispensing opening, the plunger received within the chamber so that the ribs thereof seal against an interior surface of the sidewall; and a drive member configured to drive the plunger through the chamber to the second end thereof.

17. The drug delivery assembly of claim 16, wherein a contact area of the ribs on the interior surface of the sidewall remains substantially constant while the plunger is driven through the chamber.

18. The drug delivery assembly of claim 16, wherein a trim edge of the plunger is spaced from the interior surface of the sidewall while the plunger is driven through the chamber.

19. The drug delivery assembly of claim 16, wherein the ribs are axially spaced apart from one another at least double a distance of plunger travel within the chamber during air transport.

20. The drug delivery assembly of claim 16, further comprising an intermediate rib disposed between the trailing rib and the leading rib, the intermediate rib having an annular configuration.

21. The drug delivery assembly of claim 16, wherein radial surfaces of the sidewall extending between the ribs are concavely curved along a longitudinal axis of the body portion.

22. An autoinjector device comprising:
a housing;
a syringe assembly at least partially received within the housing and including a syringe barrel with an annular sidewall extending between a first, open end and a second end having a dispensing opening;
an actuating mechanism at least partially received within the housing and including a plunger received within the syringe barrel, the plunger comprising:
- a body portion having a sidewall, a leading surface, and a trailing surface, wherein the body portion does not include a cavity having an opening defined in the trailing surface configured to receive a plunger rod therein, and a ribbed portion comprising a plurality of ribs projecting radially outwardly from the sidewall of the body portion and spaced axially apart from one another by recessed side surfaces, the plurality of ribs comprising at least a trailing rib and a leading rib, each of the ribs including an annular configuration and sized so that the ribs seal against an interior surface of the sidewall of the syringe barrel, wherein the body portion is configured to occupy a first configuration in the absence of an axial load, and a second configuration in the presence of an axial load, compression from the axial load causing the body portion in the second configuration to have an axial dimension that is less than an axial dimension of the first configuration, and wherein the ribbed portion has a first radial dimension when the body portion occupies the first configuration and a second radial dimension when the body portion occupies the second configuration, the first and second radial dimensions being substantially equal;

a drive mechanism; and a drive member configured to be driven by the drive mechanism to push the plunger through the syringe barrel to the second end thereof to thereby force a medicament within the syringe barrel through the dispensing opening.

23. The autoinjector device of claim 22, further comprising an intermediate rib disposed between the trailing rib and the leading rib, the intermediate rib having an annular configuration.

24. The autoinjector device of claim 22, wherein radial surfaces of the sidewall extending between the ribs are concavely curved along a longitudinal axis of the body portion.

25. An on-body injector device comprising:
a housing having an interior and a bottom wall within an opening extending therethrough, the housing configured to be secured to the tissue of a user;
a reservoir with an annular sidewall extending between a first, open end and a second end having a dispensing opening;
a drive mechanism including a plunger received within the reservoir, the plunger comprising:
- a body portion having a sidewall, a leading surface, and a trailing surface, wherein the body portion does not include a cavity having an opening defined in the trailing surface configured to receive a plunger rod therein, and a ribbed portion comprising a plurality of ribs projecting radially outwardly from the sidewall of the body portion and spaced axially apart from one another by recessed side surfaces, the plurality of ribs comprising at least a trailing rib and a leading rib, each of the ribs including an annular configuration and being sized so that the ribs seal against an interior surface of the sidewall of the reservoir, wherein the body portion is configured to occupy a first configuration in the absence of an axial load, and a second configuration in the presence of an axial load, compression from the axial load causing the body portion in the second configuration to have an axial dimension that is less than an axial dimension of the first configuration, and wherein the ribbed portion has a first radial dimension when the body portion occupies the first configuration and a second radial dimension when the body portion occupies the second configuration, the first and second radial dimensions being substantially equal; and a drive member configured to drive the plunger through the reservoir to the second end thereof;

an insertion mechanism including a delivery member configured to shift from a retracted position within the housing to a deployed position extending outside of the housing through the opening thereof;

a fluid pathway assembly configured to fluidly couple the reservoir to the insertion mechanism; and an actuator configured to cause the drive mechanism to drive the plunger through the reservoir to the second end thereof in response to an actuation thereof to thereby dispense medicament within the reservoir through the insertion mechanism.

26. The on-body injector device of claim 25, further comprising an intermediate rib disposed between the trailing rib and the leading rib, the intermediate rib having an annular configuration.

27. The on-body injector device of claim 25, wherein radial surfaces of the sidewall extending between the ribs are concavely curved along a longitudinal axis of the body portion.

* * * * *

UNITED STATES PATENT AND TRADEMARK OFFICE
CERTIFICATE OF CORRECTION

| | | |
|---|---|---|
| PATENT NO. | : 11,191,904 B2 | Page 1 of 1 |
| APPLICATION NO. | : 16/154759 | |
| DATED | : December 7, 2021 | |
| INVENTOR(S) | : Julian Jazayeri et al. | |

It is certified that error appears in the above-identified patent and that said Letters Patent is hereby corrected as shown below:

In the Specification

At Column 4, Line 9, "disclosure; and" should be -- disclosure; --.

At Column 7, Line 12, "L" should be -- L. --.

In the Claims

At Column 26, Line 62, "wherein the" should be -- wherein --.

Signed and Sealed this
Twenty-eighth Day of June, 2022

Katherine Kelly Vidal
*Director of the United States Patent and Trademark Office*